(12) United States Patent
Fields et al.

(10) Patent No.: US 10,722,443 B2
(45) Date of Patent: Jul. 28, 2020

(54) MOISTURIZING COMPOSITIONS AND USES THEREOF

(71) Applicant: RODAN & FIELDS, LLC, San Francisco, CA (US)

(72) Inventors: Kathy Ann Fields, San Francisco, CA (US); Kathryn Pregerson Rodan, Oakland, CA (US); George Paul Majewski, Emeryville, CA (US); Timothy John Falla, Woodinville, WA (US); Dzung Q. Le, Berkeley, CA (US)

(73) Assignee: RODAN & FIELDS, LLC, San Francisco, CA (US)

( * ) Notice: Subject to any disclaimer, the term of this patent is extended or adjusted under 35 U.S.C. 154(b) by 0 days.

(21) Appl. No.: 15/430,578

(22) Filed: Feb. 13, 2017

(65) Prior Publication Data

US 2018/0071193 A1 Mar. 15, 2018

Related U.S. Application Data

(60) Provisional application No. 62/394,540, filed on Sep. 14, 2016.

(51) Int. Cl.

| | |
|---|---|
| *A61Q 19/00* | (2006.01) |
| *A61K 8/73* | (2006.01) |
| *C08B 37/08* | (2006.01) |
| *C08B 37/00* | (2006.01) |
| *C08B 11/04* | (2006.01) |
| *A61K 31/327* | (2006.01) |
| *A61K 9/06* | (2006.01) |
| *C08L 89/00* | (2006.01) |
| *A61K 8/64* | (2006.01) |
| *A61K 9/00* | (2006.01) |
| *C08L 5/08* | (2006.01) |
| *A61K 47/02* | (2006.01) |
| *A61K 45/06* | (2006.01) |

(52) U.S. Cl.
CPC .................. *A61K 8/73* (2013.01); *A61K 8/64* (2013.01); *A61K 8/731* (2013.01); *A61K 8/732* (2013.01); *A61K 8/733* (2013.01); *A61K 8/735* (2013.01); *A61K 8/736* (2013.01); *A61K 8/737* (2013.01); *A61K 9/0048* (2013.01); *A61K 9/06* (2013.01); *A61K 31/327* (2013.01); *A61K 45/06* (2013.01); *A61K 47/02* (2013.01); *A61Q 19/005* (2013.01); *A61Q 19/007* (2013.01); *C08B 37/006* (2013.01); *C08B 37/0072* (2013.01); *C08L 5/08* (2013.01); *C08L 89/00* (2013.01); *A61K 2800/594* (2013.01); *C08L 2203/02* (2013.01); *C08L 2205/025* (2013.01); *C08L 2205/03* (2013.01); *C08L 2205/035* (2013.01); *C08L 2205/04* (2013.01)

(58) Field of Classification Search
None
See application file for complete search history.

(56) References Cited

U.S. PATENT DOCUMENTS

| | | | | |
|---|---|---|---|---|
| 6,077,916 | A * | 6/2000 | Laurencin | A61L 27/26 424/422 |
| 6,224,893 | B1 * | 5/2001 | Langer | A61K 9/0019 424/423 |
| 6,486,232 | B1 * | 11/2002 | Wise | A61B 17/866 523/118 |
| 2006/0275238 | A1 * | 12/2006 | Blasko-Begoihn | A61K 8/73 424/70.13 |
| 2007/0197754 | A1 * | 8/2007 | White | A61L 27/52 527/300 |
| 2008/0003192 | A1 | 1/2008 | Modi | |
| 2008/0160088 | A1 | 7/2008 | Mackowiak | |
| 2011/0053270 | A1 * | 3/2011 | Chang | C12N 5/0068 435/402 |
| 2014/0142190 | A1 | 5/2014 | Piron et al. | |
| 2014/0199250 | A1 | 7/2014 | Wang et al. | |

FOREIGN PATENT DOCUMENTS

WO 2017139765 A1 8/2017

OTHER PUBLICATIONS

Miquelard-Garnier, Guillaume, et al. "Synthesis and rheological behavior of new hydrophobically modified hydrogels with tunable properties." Macromolecules 39.23 (2006): 8128-8139.*
"Healthy Aging—the best anti-aging ingredients in skincare"; http://antiagingboomer.com/healthy-aging-the-best-anti-aging-ingredients-in-skincare/; Mar. 14, 2011 version from web.archive.org/web/20110314072405/http://antiagingboomer.com:80/healthy-aging-the-best-anti-aging-ingredients-in-skincare (Year: 2011).*
Martin, Lee, et al. "The release of model macromolecules may be controlled by the hydrophobicity of palmitoyl glycol chitosan hydrogels." Journal of controlled release 80.1-3 (2002): 87-100. (Year: 2002).*
Matricardi, P., et al. "Semi-IPN hydrogel based on scleroglucan and alginate: drug delivery behavior and mechanical characterisation." Journal of drug delivery science and technology 17.3 (2007): 193-197. (Year: 2007).*
Sperling, L. H. "Interpenetrating polymer networks: an overview." 1994. 3-38. (Year: 1994).*
Lohani et al. "Interpenetrating Polymer Networks as Innovative Drug Delivery Systems" (May 14, 2014) J. Drug Delivery 2014:583612 (11 pages).
International Search Report and Written Opinion for PCT/US2017/017671 dated Jun. 9, 2017.

(Continued)

*Primary Examiner* — Nissa M Westerberg

(74) *Attorney, Agent, or Firm* — Pepper Hamilton LLP

(57) ABSTRACT

Embodiments herein are directed to moisturizing compositions comprising interpenetrating polymer networks, methods of making moisturizing compositions and methods of using moisturizing compositions.

16 Claims, 20 Drawing Sheets

(2 of 20 Drawing Sheet(s) Filed in Color)

(56) References Cited

OTHER PUBLICATIONS

Majewski et al., "Characterization of bound water in skin hydrators prepared with and without a 3D3P interpenetrating polymer network", Aug. 16, 2018, Skin Res. Technol., 25(2):150-157.
Palleschi et al., "Investigation on a New Scleroglucan/Borax Hydrogel: Structure and Drug Release", available online May 22, 2006, Int. J. Pharma., 322(1-2):13-21.
European Supplemental Search Report for EP 17750964 dated Jul. 18, 2019.

* cited by examiner

Before

After

Baseline

8 Weeks After Treatment

MOISTURIZING COMPOSITIONS AND USES THEREOF

CROSS-REFERENCE TO RELATED APPLICATIONS

This application claims priority to U.S. Provisional Patent Application No. 62/294,706 filed on Feb. 12, 2016, and U.S. Provisional Patent Application No. 62/394,540 filed on Sep. 14, 2016, the disclosures of which are incorporated by reference in their entireties.

SUMMARY

Embodiments herein are directed to moisturizing compositions comprising: an interpenetrating polymer network made up of a crosslinked polypeptide or polysaccharide; a branched polymer with a hydrophobic modification; and a linear polypeptide or polysaccharide. In some embodiments, the composition is an interpenetrating polymer network comprising a crosslinked polypeptide or polysaccharide; a branched polymer with a hydrophobic modification; and a linear polypeptide or polysaccharide, wherein the crosslinked polypeptide or polysaccharide entraps the interlaced branched polymer with a hydrophobic modification and the linear polypeptide or polysaccharide to form the interpenetrating polymer network.

Some embodiments are directed to methods of treating dry and/or irritated skin comprising administering a moisturizing composition comprising: an interpenetrating polymer network made up of a crosslinked polypeptide or polysaccharide; a branched polymer with a hydrophobic modification; and a linear polypeptide or polysaccharide.

Some embodiments are directed to a method of producing an interpenetrating polymer network moisturizing composition, the method comprising: dispersing a non-crosslinked polypeptide or polysaccharide capable of crosslinking in water to form a first phase; combining a linear polypeptide or polysaccharide and a branched polymer with a hydrophobic modification with a humectant to form a second phase; combining the first and second phases to form a third phase of uncrosslinked interlaced polymers, polypeptides, or polysaccharides; adding a mono-valent ion, di-valent ion or a combination thereof to the third phase to crosslink one or more polypeptide, polymer, or polysaccharide to form an interpenetrating polymer network moisturizing composition.

BRIEF DESCRIPTION OF THE FIGURES

The file of this patent contains at least one photograph or drawing executed in color. Copies of this patent with color drawings or photographs will be provided by the Office upon request and payment of necessary fee.

FIG. 9 depicts improvements in clinical grading.

FIG. 11 depicts 3 different subjects and the change in mean corneometer measurements over the course of the study.

FIG. 14 depicts the improvement in the skin as subjectively reported by each individual.

DETAILED DESCRIPTION

Figure 1:
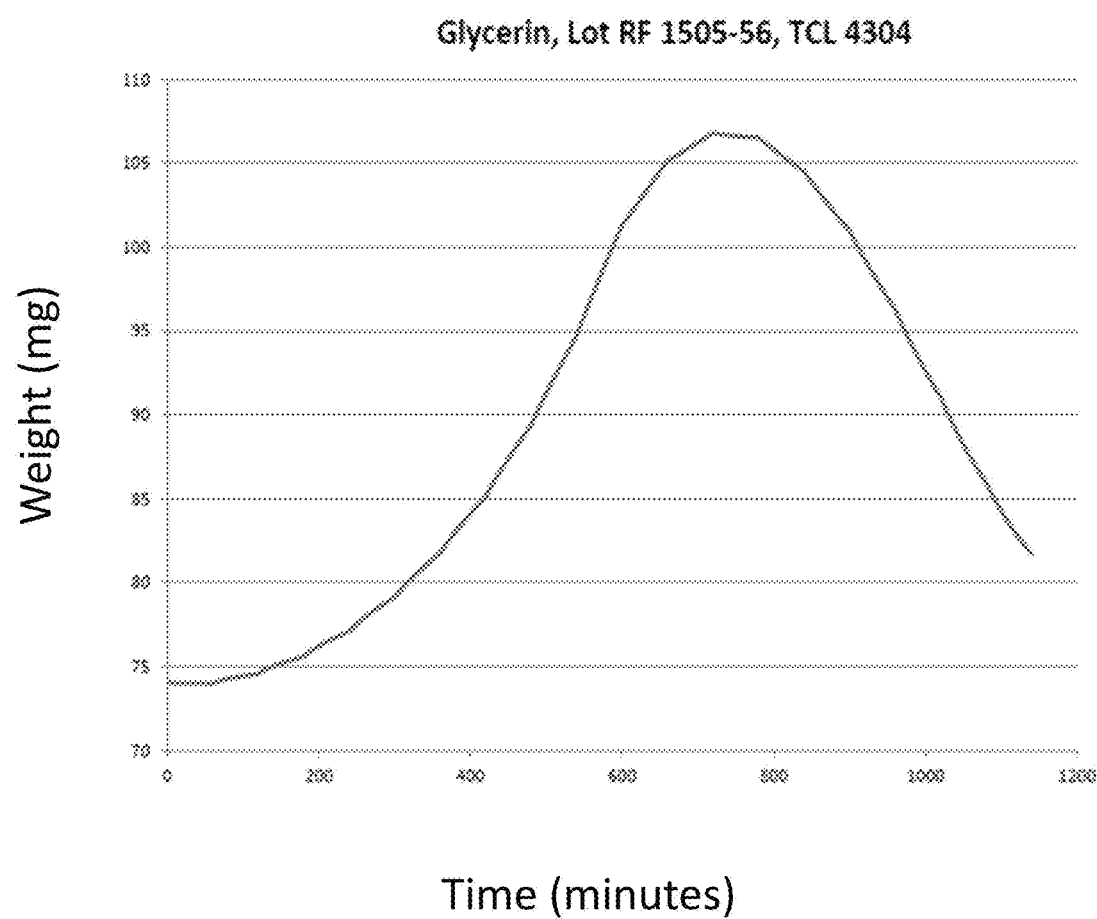
FIG. 1 depicts the DVS weight versus time curve for formulation 1505-56.
Figure 2:
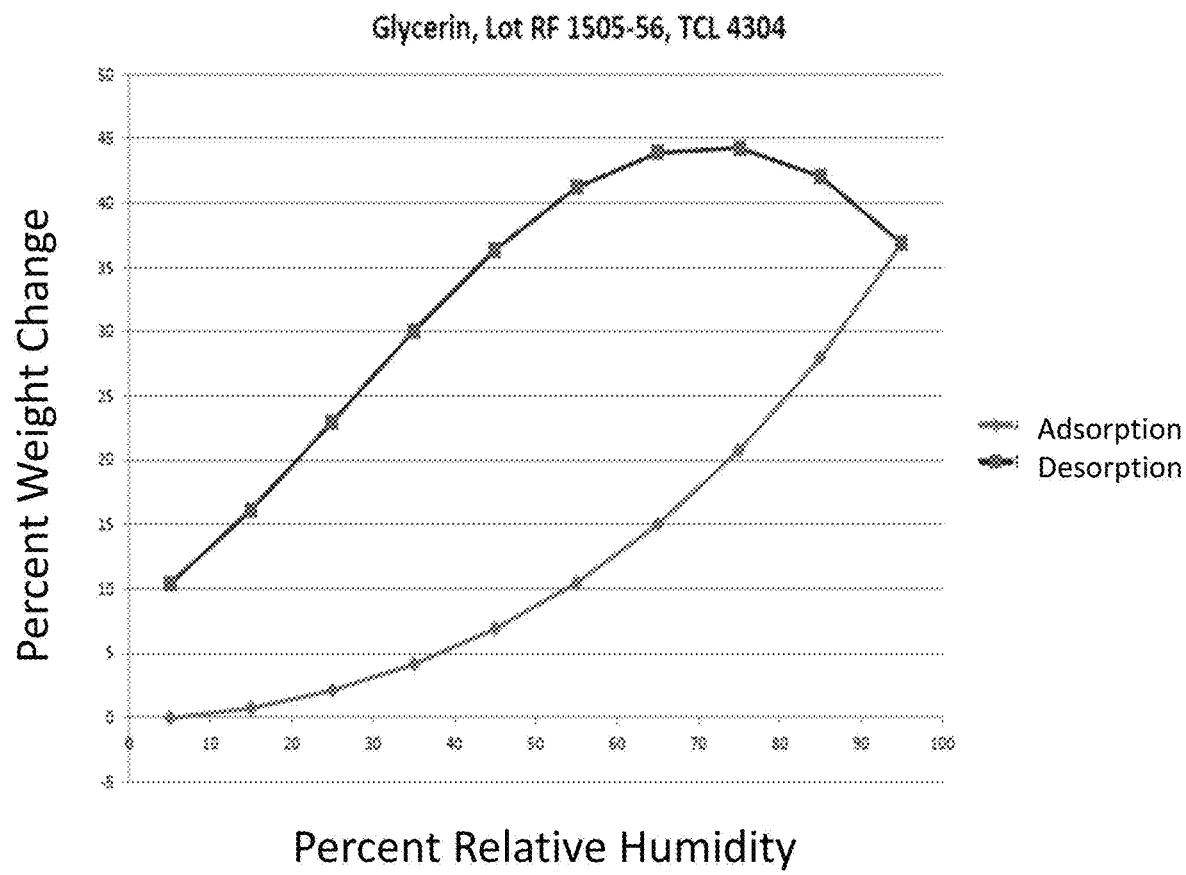
FIG. 2 depicts the DVS weight change versus percent relative humidity curve for formulation 1505-56.
Figure 3:
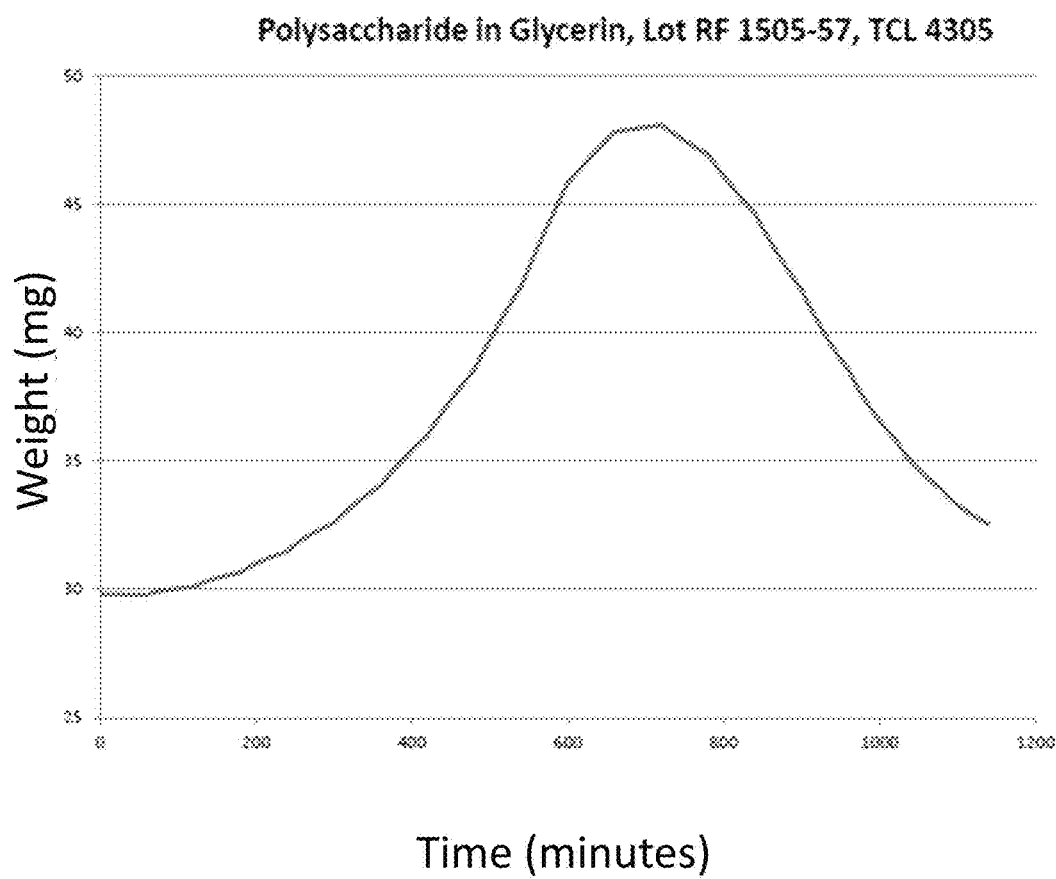
FIG. 3 depicts the DVS weight versus time curve for formulation 1505-57.
Figure 4:
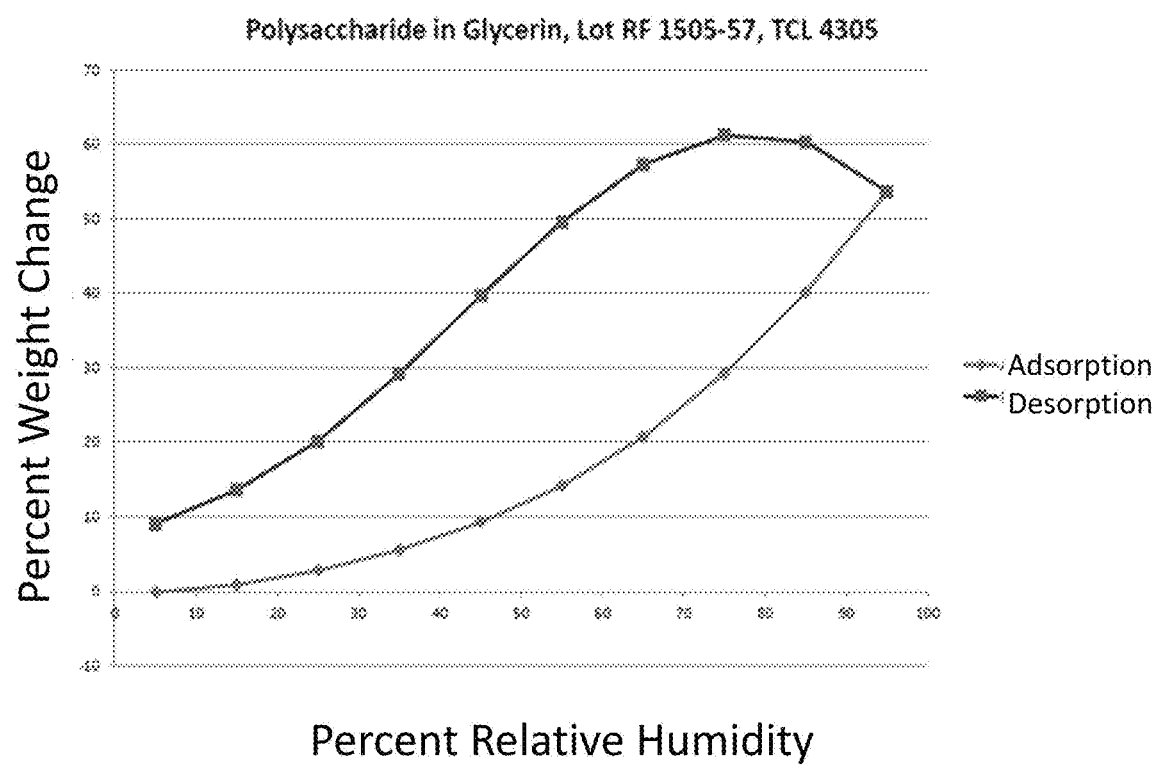
FIG. 4 depicts the DVS weight change versus percent relative humidity curve for formulation 1505-57.
Figure 5:
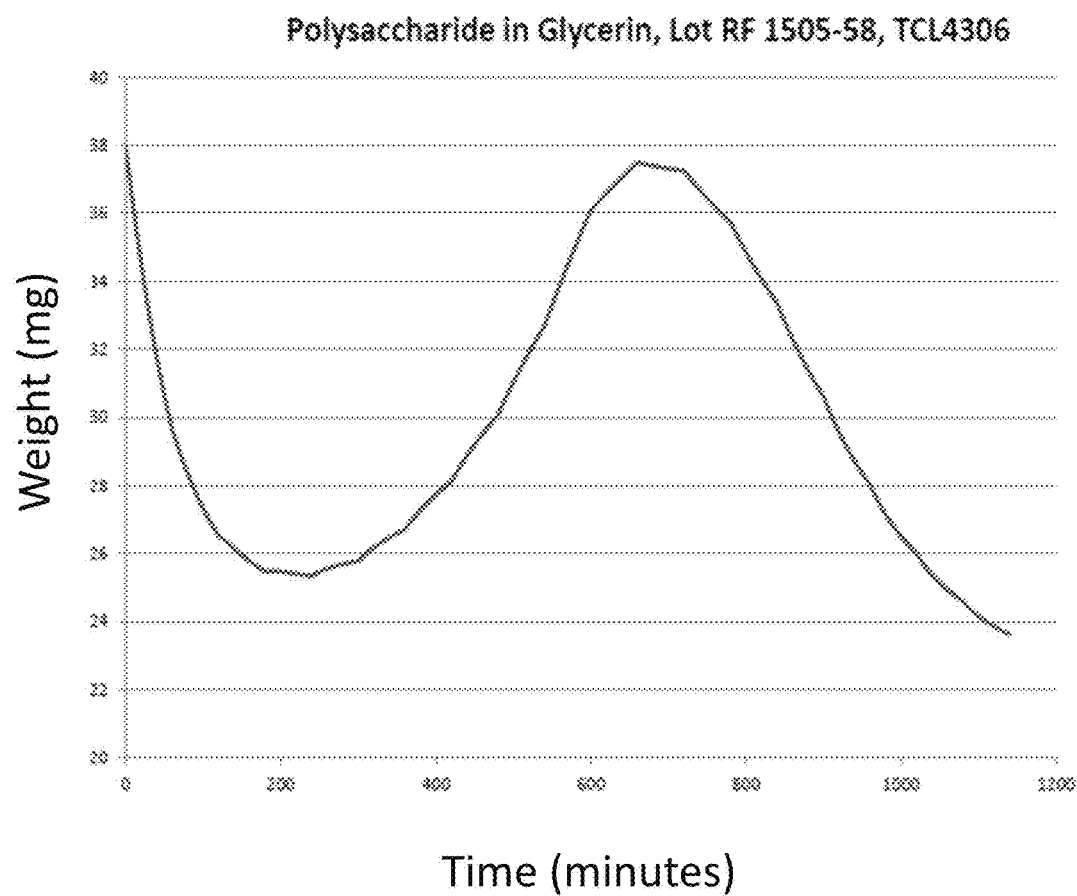
FIG. 5 depicts the DVS weight versus time curve for formulation 1505-58.
Figure 6:
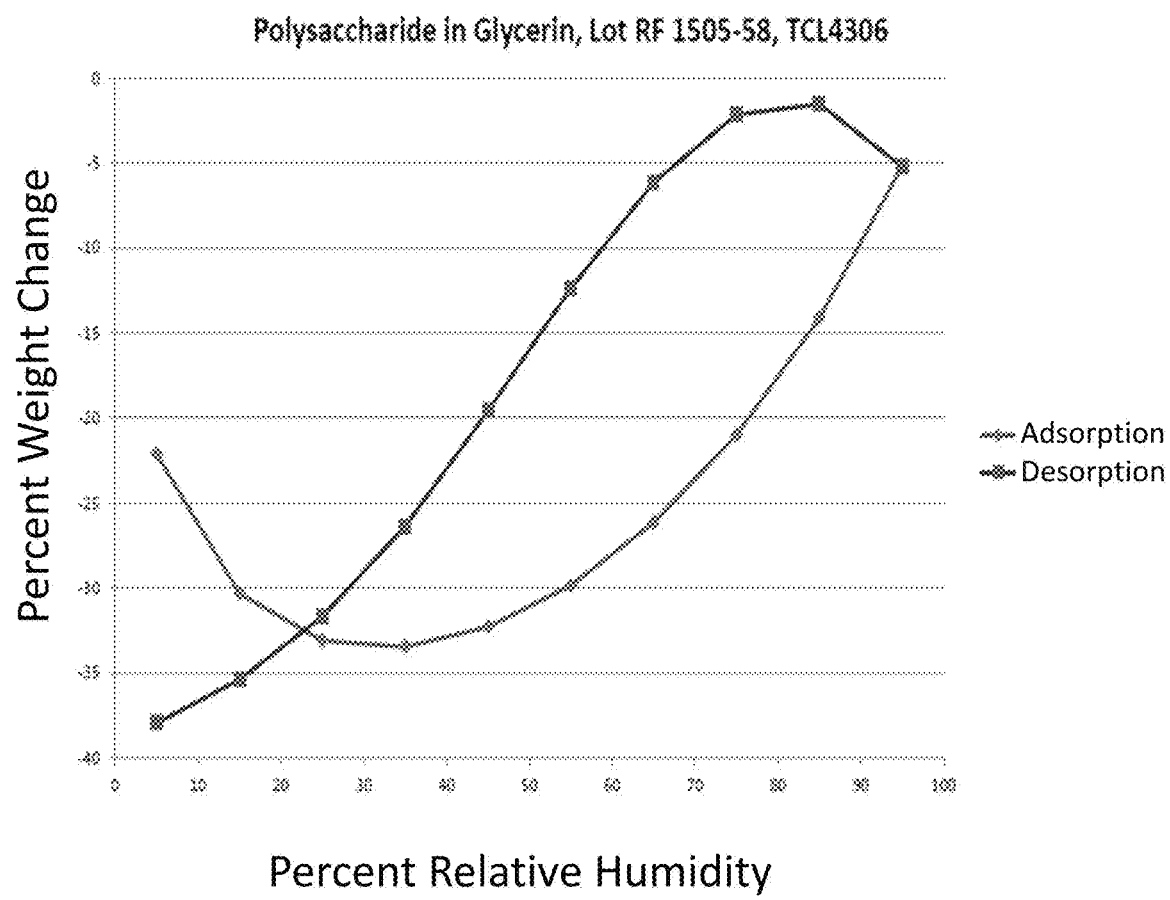
FIG. 6 depicts the DVS weight change versus percent relative humidity curve for formulation 1505-58.
Figure 7:
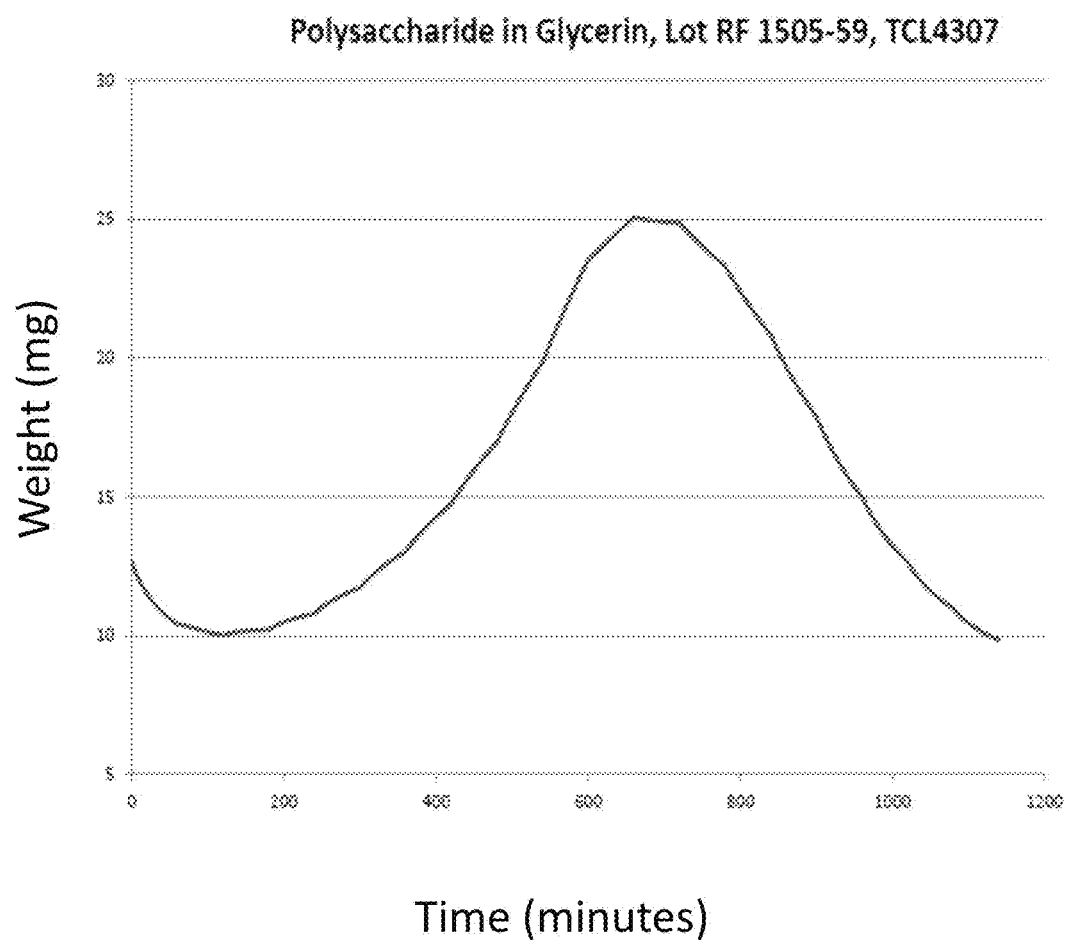
FIG. 7 depicts the DVS weight versus time curve for formulation 1505-59.
Figure 8:
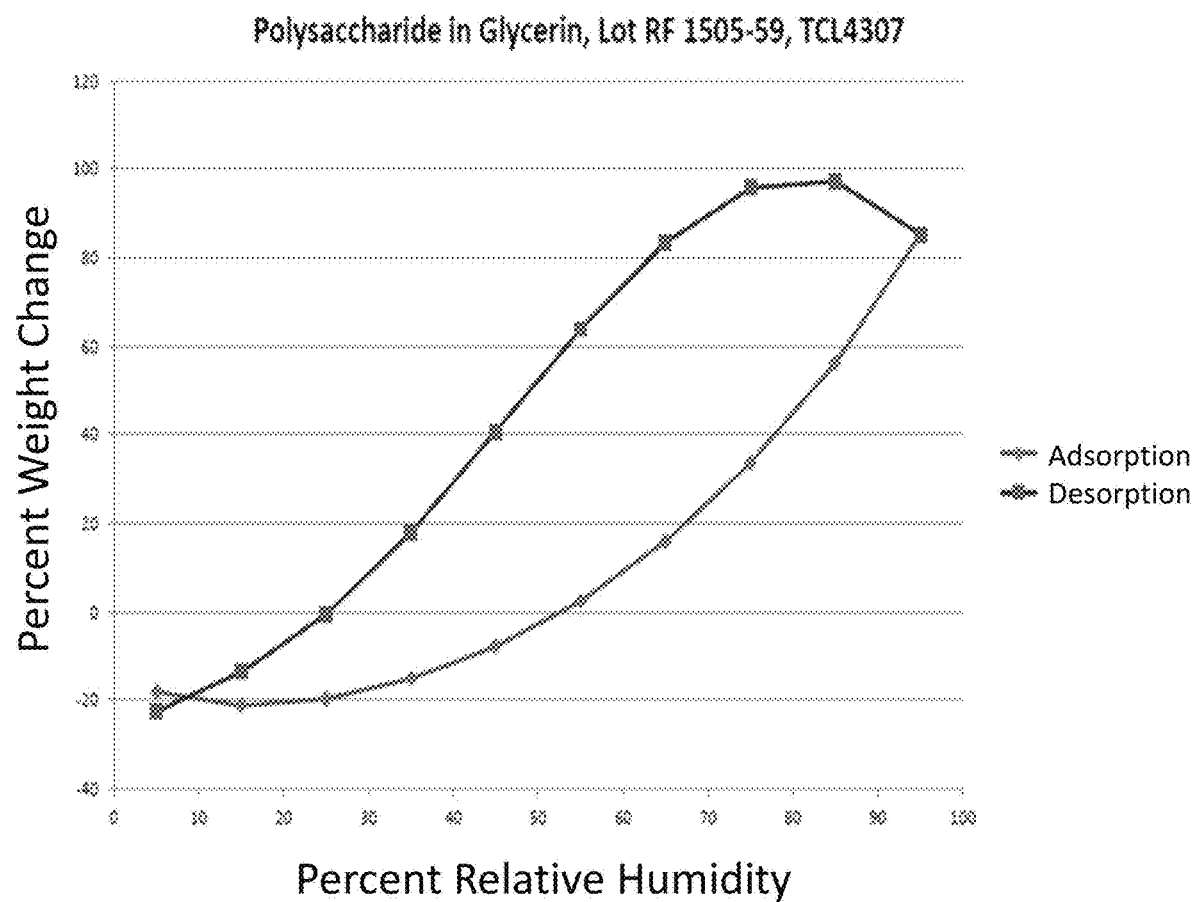
FIG. 8 depicts the DVS weight change versus percent relative humidity curve for formulation 1505-59.

Traditional methods of hydrating skin (especially facial skin) are not sufficient especially in dry weather conditions. Commonly formulated barrier forming occlusive agents (petrolatum, high MW silicone fluids, plant butters) work well for reducing trans epidermal water loss but these materials exhibit some undesired properties including the increased potential of comedogenicity (clogging of pores). Occlusive materials also do not attract/accumulate water at the skin's surface which is limiting if one is trying to immediately improve the surface hydration of human skin. Commonly formulated humectants (i.e. glycols, glycerin, hyaluronic acid, or PCA salts) attract water to the skin's surface but these materials also exhibit undesirable properties which can include a lingering tackiness or stickiness and product pilling or flaking off skin. As a result humectants are often formulated at use levels far below 10% in moisturizing skin care products. There is a need to increase concentrations of humectant and osmolytic ingredients to achieve a more significant and immediate hydrating effect which can alter skin's appearance by plumping dry skin to visibly reduce the appearance of wrinkles. Improvements can be made with moisture binding polysaccharides such as, but not limited to hyaluronic acid to increase deposition and/or adherence and interaction on the skin's surface.

Without wishing to be bound by theory, the compositions of the present invention cannot be formed by merely mixing the individual components together; such a method would produce a composition with a different structure and having a much lower viscosity than is desirable. For example, the dynamic viscosity of the same polymers at the same concentrations in the same solvent system without an interpenetrating polymer network is between 100-300 cps. Embodiments of present compositions are formed when the method steps described in the embodiments herein are followed. The order of the steps described herein produce an interpenetrating polymer network (IPN) with beneficial properties as described herein. In embodiments, the linear polypeptide or polysaccharide and branched polymer with a hydrophobic modification are mixed together first and must interlace, the non-crosslinked polypeptide or polysaccharide capable of being crosslinked is then added to the mixture of the linear polypeptide or polysaccharide and branched polymer with a hydrophobic modification e before the crosslinking can be initiated. Upon the addition of divalent salts and cooling, the crosslinkable polypeptide or polysaccharide becomes crosslinked and entraps the other ingredients, thereby forming the IPN. In embodiments, the dynamic viscosity of the claimed IPN of the present invention is much greater than the viscosity of the individual components simply mixed together and is between about 400-1400 cps. This resulting IPN has a thixotropic rheology with a substantive skin feel on application which provides the beneficial properties described in the embodiments herein. Embodiments herein are directed to moisturizing composition comprising: an interpenetrating polymer network made up of a crosslinked polypeptide or polysaccharide; a branched polymer with a hydrophobic modification; and a linear polypeptide or polysaccharide. In some embodiments the composition is an interpenetrating polymer network comprising a crosslinked polypeptide or polysaccharide; a branched polymer with a hydrophobic modification; and a linear polypeptide or polysaccharide, wherein the crosslinked polypeptide or polysaccharide entraps the interlaced branched polymer with a hydrophobic modification and the linear polypeptide or polysaccharide to form the interpenetrating polymer network. In some embodiments, the interpenetrating polymer network is a de-tackified interpenetrating polymer network for topical humectant delivery. In some embodiments, the compositions described herein can be used to treat and/or prevent dry skin by delivering agents known to promote normalization of epidermal proliferation and differentiation such as but not limited to calcium PCA, phosphatidylglycerol, and mixtures of ceramides. In some embodiments, the compositions described herein have superior sensorial properties and water binding properties. In yet other embodiments, the compositions described herein lack the undesired sensorial tackiness associated with dry-down during application of typical hydrogels. As a result, the compositions described herein deliver a superior sensorial experience during application.

Dry skin is a persistent problem and especially aggravated in low relative humidity conditions and during seasonal weather transitions. The biological implications with regard to keratinocyte under-differentiation and over proliferation in dry skin have recently come to light and there is a need for more concentrated delivery of humectants in a cosmetically suitable preparation. The compositions have unique physical properties (hydrophobic-like, adhesive, non-sticky, quick spreading, film forming with high affinity for the skin's surface) to aid the delivery of humectants capable of dissolving desmosomes to assist in desquamation and deliver other agents which promote the differentiation of keratinocytes to normalize over proliferation associated with dry skin.

The use of humectants for improving surface moisture levels of human skin is well established in the art of skin care formulation. This practice includes a wide range of both polymeric and non-polymeric substances. Having a high affinity for water, humectant substances absorb and retain water from air. Typically humectant substances which are commonly applied on skin for hydration benefits consist of compounds with hydrophilic groups including hydroxyl, amine, carboxyl and salts. One challenge in applying these materials to human skin includes the undesired sensorial effects of stickiness or tackiness which accompany the most popular topical humectants including hyaluronic acid and glycerin. While the FDA identifies glycerin formulated at 30% as an OTC skin protectant it is rare to find commercially available products which utilize glycerin at 10% or above. Equally many humectant polysaccharides including hyaluronic acid are only utilized at minimal levels in skin care formulations to also avoid the undesired sensorial properties of glue-like stickiness and tackiness which is inherent in these gum-like substances. A need exists for treating dry skin with more significant concentrations of humectants with minimized stickiness and tackiness to alleviate dry skin for prolonged periods without the need of constant product reapplications.

The present invention is directed to compositions including, and methods of preparing, an interpenetrating polymer network capable of topically delivering extremely high levels of humectants with significantly minimized undesired stickiness and a superior sensorial experience. The present invention is also directed to the use of these compositions to treat and/or prevent dry and/or irritated skin. More specifically, the inventors have identified the correct balance/ratio of carboxyl groups to hydroxyl groups which alter the aesthetic sensorial properties of both the polymer and non-polymer humectants such as, but not limited to glycerin and hyaluronic acid while in the context of a 3-dimensional interlaced polymer network. As a result, humectants, such as, but not limited to, glycerin, can be applied to the skin at concentrations of 30% or above without the undesired effects of stickiness to yield significant and prolonged hydration of dry and irritated skin.

Although any methods and materials similar or equivalent to those described herein can be used in the practice or testing of embodiments of the present invention, the exemplary methods, devices, and materials are now described.

The term "comprising" means "including, but not limited to." The term "consisting essentially of" means the method or composition includes the steps or components specifically recited, and may also include those that do not materially affect the basic and novel characteristics of the present invention. The term "consisting of" means the method or composition includes only the steps or components specifically recited.

In each of the embodiments disclosed herein, the compounds and methods may be utilized with or on a subject in need of such treatment, which may also be referred to as "in need thereof." As used herein, the phrase "in need thereof" means that the subject has been identified as having a need for the particular method or treatment and that the treatment has been given to the subject for that particular purpose.

As used herein, the term "Interpenetrating polymer network" (IPN) means a polymer comprising two or more networks which are at least partially interlaced on a polymer/molecular scale but not covalently bonded to each other and cannot be separated unless chemical bond(s), for example, in at least one of the networks, are broken. In some embodiments, the two or more networks can be envisioned to be entangled in such a way that they are concatenated and cannot be pulled apart, but not bonded to each other by any chemical bond. In other words, an Interpenetrating Polymer Network (IPN) is to a scaffold or three dimensional structure that is formed by the processes described herein. The IPN is composed of one or more crosslinked polymer, polypeptide or polysaccharide and one or more polymer, polypeptide, polysaccharide, or other agent which have been entrapped within the crosslinked polymer, polypeptide or polysaccharide A mixture of two or more pre-formed polymer networks is not an IPN.

As used herein, the term "crosslinked" refers to the ionic bond formed and change in tertiary structure of the polymer, polypeptide or polysaccharide upon the addition of mono- or di-valent ions to and cooling of the third phase to form the IPN.

As used herein, the term or phrase "crosslinkable" or "non-crosslinked capable of crosslinking" refers to the polymer, polypeptide or polysaccharide in its initial state before the crosslinking process has occurred.

As used herein, a "semi-interpenetrating polymer network" (SIPN): means a polymer comprising one or more networks and one or more linear or branched polymer(s) characterized by the penetration on a molecular scale of at least one of the networks by at least some of the linear or branched macromolecules. Semi-interpenetrating polymer networks are distinguished from interpenetrating polymer networks because the constituent linear or branched polymers can, in principle, be separated from the constituent polymer network(s) without breaking chemical bonds; they are polymer blends.

As used herein, a "sequential interpenetrating polymer network" means an interpenetrating polymer network prepared by a process in which the second component network is formed following the formation of the first component network.

As used herein, a "sequential semi-interpenetrating polymer network" means a semi-interpenetrating polymer network prepared by a process in which the linear or branched components are formed following the completion of the reactions that lead to the formation of the network(s) or vice versa.

As used herein, the term "patient" and "subject" are interchangeable and may be taken to mean any living organism, which may be treated with compounds of the present invention. As such, the terms "patient" and "subject" may include, but is not limited to, any non-human mammal, primate or human. In some embodiments, the "patient" or "subject" is an adult, child, infant, or fetus. In some embodiments, the "patient" or "subject" is a human. In some embodiments, the "patient" or "subject" is a mammal, such as mice, rats, other rodents, rabbits, dogs, cats, swine, cattle, sheep, horses, primates, or humans.

As used herein, the terms "adjunctive administration" and "adjunctively" may be used interchangeably, and refer to simultaneous administration of more than one compound in the same dosage form, simultaneous administration in separate dosage forms, and separate administration of more than one compound as part of a single therapeutic regimen.

As used herein the term 'topical formulation' refers to a formulation that may be applied to skin or a mucosa. Topical formulations may, for example, be used to confer therapeutic benefit to a patient or cosmetic benefits to a consumer. Topical formulations can be used for both topical and transdermal administration of substances.

The term 'topical administration' is used in its conventional sense to mean delivery of a substance, such as a therapeutically active agent, to the skin or a localized region of the body.

The term 'transdermal administration' is used to mean administration through the skin. Transdermal administration is often applied where systemic delivery of an active is desired, although it may also be useful for delivering an active to tissues underlying the skin with minimal systemic absorption.

Before the present compositions and methods are described, it is to be understood that this invention is not limited to the particular processes, compositions, or methodologies described, as these may vary. Moreover, the processes, compositions, and methodologies described in particular embodiments are interchangeable. Therefore, for example, a composition, dosages regimen, route of administration, and so on described in a particular embodiments may be used in any of the methods described in other particular embodiments. It is also to be understood that the terminology used in the description is for the purpose of describing the particular versions or embodiments only, and is not intended to the limit the scope of the present invention which will be limited only by the appended claims. Unless defined otherwise, all technical and scientific terms used herein have the same meanings as commonly understood by one of the ordinary skill in the art. Although any methods similar or equivalent to those describe herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

It must be noted that, as used herein, and in the appended claims, the singular forms "a", "an" and "the" include plural reference unless the context clearly dictates otherwise.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the described includes instances where the event occurs and instances where it does not.

"Administering" when used in conjunction with a therapeutic means to administer a therapeutic directly or indirectly into or onto a target tissue to administer a therapeutic to a patient whereby the therapeutic positively impacts the tissue to which it is targeted. "Administering" may include the act of self-administration or administration by another person such as a health care provider.

The term "improves" is used to convey that the present invention changes either the appearance, form, characteristics, structure, function and/or physical attributes of the tissue to which it is being provided, applied or administered. "Improves" may also refer to the overall physical state of an individual to whom an active agent has been administered. For example, the overall physical state of an individual may "improve" if one or more symptoms of the disease, condition or disorder are alleviated by administration of an active agent.

The term "cosmetic" means an agent utilized, and/or intended to be applied to the human body for cleansing, beautifying, promoting attractiveness, altering the appearance of the skin or any combination thereof.

The terms "effective amount" or "effective dose" as used herein are interchangeable and may refer to the amount of an active agent or compound or composition that has the effect of moisturizing, cleansing, beautifying, promoting attractiveness, altering the appearance of the skin, or any combination thereof, that is being sought by the user. In some embodiments, "effective amount" or "effective dose" as used herein are interchangeable and may refer to the amount of an active agent or compound or composition that has the effect of promoting the exfoliation of dry skin, promoting the digestion of desmosomes, normalizing cell maturation, modulating keratinocyte function, normalizing keratinocyte differentiation, normalizing keratinocyte proliferation, modulating phosphatidylglycerol content of keratinocytes, modulating and/or improving the moisture content of the skin, promoting the retention of long lasting hydration in the skin, increasing skin moisture, improving skin water balance, increasing skin hydration, decreasing transepidermal water loss, reducing evaporation of water from the skin, treating and/or preventing dry and/or irritated skin, defending against, and reducing visible signs of aging for noticeably firmer, smoother, and flawless looking skin, erasing the appearance of premature aging, including brown spots, dullness and discoloration, visibly brightening the skin, reducing the appearance of fine lines and wrinkles, creating a radiant complexion, shielding the skin again biological and environmental aggressors associated with dry, irritated and sensitive skin, helping the skin retain moisture and remain comfortable when challenged by climate and other environmental aggressors, rehydrating the skin, to repairing, renewing, and/or enhancing the skin's natural moisture barrier.

The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to alleviating the symptoms associated with the specific disorder, disease or condition. In some embodiments, the term refers to alleviating the symptoms associated with the specific disorder, disease or condition. In some embodiments, the term refers to restoring function which was impaired or lost due to a specific disorder, disorder or condition.

The term "inhibit," "suppress," "decrease," "interfere," and/or "reduce" (and like terms) generally refers to the act of reducing, either directly or indirectly, a function, activity, or behavior relative to the natural, expected, or average or relative to current conditions.

The term "increase," "enhance," "stimulate," and/or "induce" (and like terms) generally refers to the act of improving or increasing, either directly or indirectly, a function or behavior relative to the natural, expected, or average or relative to current conditions.

The term "modulate," "modify," and/or "modulator" generally refers to the act of directly or indirectly promoting/stimulating or interfering with/inhibiting a specific function or behavior. In some instances a modulator may increase and/or decrease a certain activity or function relative to its natural state or relative to the average level of activity that would generally be expected or relative to a current level of activity.

As used herein, the term "normalize" refers to the act of establishing and/or maintaining a relative balance or equilibrium between two or more activities, functions or conditions.

The term "cosmetic composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "topically" and "topical" refers to application of the compositions of the present invention to the surface of the skin and mucosal cells and tissues.

Embodiments herein are directed to moisturizing compositions consisting essentially of: an interpenetrating polymer network made up of a crosslinked polypeptide or polysaccharide; a branched polymer with a hydrophobic modification; and a linear polypeptide or polysaccharide. Embodiments herein are directed to moisturizing compositions consisting of: an interpenetrating polymer network made up of a crosslinked polypeptide or polysaccharide; a branched polymer with a hydrophobic modification; and a linear polypeptide or polysaccharide. Embodiments herein are directed to moisturizing compositions comprising: an interpenetrating polymer network made up of a crosslinked polypeptide or polysaccharide; a branched polymer with a hydrophobic modification; and a linear polypeptide or polysaccharide. In some embodiments, the composition is an interpenetrating polymer network comprising a crosslinked polypeptide polysaccharide; a branched polymer with a hydrophobic modification; and a linear polypeptide or polysaccharide, wherein the crosslinked polypeptide or polysaccharide entraps the interlaced branched polymer with a hydrophobic modification and the linear polypeptide or polysaccharide to form the interpenetrating polymer network. In some embodiments, the polypeptide or polysaccharide capable of crosslinking, the branched polymer with a hydrophobic modification and the linear polypeptide or polysaccharide form an interpenetrating polymer network.

In some embodiments, the compositions described herein comprising interpenetrating polymer networks act as a moisture delivery scaffold for water, glycerin, other small molecule humectants and osmolytes which can be introduced at high concentrations of about 30-45% of the total composition. In some embodiments, the ratio of the humectants to the interpenetrating polymer networks in the compositions described herein is very important and unique as it may alter the physical properties in a way which confers to the composition more hydrophobic characteristics. Without wishing to be bound by theory, the hydroxyl groups of glycerin and glycols hydrogen bond with the hydroxyl groups of the polysaccharides to a point where the hydrogen-bonding groups satisfy each other. Thus, in some embodiments, the compositions described herein have a sensorial skin feel which is more like a slippery silicone oil which exhibits no stickiness, tackiness or pilling. After product dry down on skin, water applied starts to bead as though the composition was prepared from hydrophobic oils or waxes. In some embodiments, the compositions described herein have other unique physical properties including, but not limited to, an increase gelling and viscosity with the addition of cosmetic grade acids (e.g. lactic acid, citric acid, glycolic acid). It is common knowledge that most cosmetic gel structures decrease in viscosity with the addition of acids. The unique physical properties achieved from the compositions described herein allow for delivering high levels of humectants which behave partially like occlusive barrier agents. In some embodiments, the compositions described herein have a high deposition characteristic on glass, plastic and human skin. In some embodiments, the compositions described herein demonstrate a significant improvement in surface hydration of human skin even 8 hours after application. In some embodiments, the compositions described herein are capable of delivering agents which promote keratinocyte differentiation.

In some embodiments, the compositions described herein comprising interpenetrating polymer networks act as a drug or active ingredient delivery scaffold for skin treatments, acne treatments, wrinkle treatments, or anti-inflammatory agents, In some embodiments, the acne treatment is selected from the group consisting of benzoyl peroxide, salicylic acid, willowbark extract, poly hydroxyacid, tannic acid, hydroxybenzoic acid, juniperic acid, tartaric acid, glycolic acid, lactic acid, and citric acid. In some embodiments, the wrinkle treatment is selected from the group consisting of retinol, antioxidants, vitamin A, retinoid, tretinoin, and tazarotene. In some embodiments, the anti-inflammatory agent is selected from the group consisting of ibuprofen, diclofenac, felbinac, ketoprofen, and piroxicam.

Embodiments herein are directed to a delivery system comprising an interpenetrating polymer network made up of a crosslinked polypeptide or polysaccharide; a branched polymer with a hydrophobic modification; a linear polypeptide or polysaccharide; and an active ingredient; wherein the crosslinked polypeptide or polysaccharide entraps the interlaced branched polymer with a hydrophobic modification and the linear polypeptide or polysaccharide to form the interpenetrating polymer network.

In some embodiments, the crosslinked polypeptide or polysaccharide is selected from the group consisting of crosslinked gellan gum, crosslinked carrageenan, crosslinked chitosan, crosslinked xanthan gum, sodium polyglutamate crosspolymer, polydextrose, and combinations thereof. In some embodiments, the crosslinked polypeptide or polysaccharide is crosslinked gellan gum.

In some embodiments, interpenetrating polymer networks such as those described herein can be used to deposit and/or deliver agents such as, but not limited to, water, humectants, natural moisturizing factors, osmolytes, bio-active hydrators, and keratinocyte differentiation promoting agents. In some embodiments, surface spreading and contact with skin is improved when the interpenetrating polymer network comprises a hydrophobically modified polymer.

In some embodiments, the branched polymer with a hydrophobic modification is selected from the group consisting of hydrophobically modified hydroxypropylmethylcellulose, hydrophobically modified cetyl hydroxy propyl methyl cellulose, hydrophobically modified sodium acetyl hyaluronate, hydrophobically modified cetyl hydroxyethylcellulose, hydrophobically modified starch, hydrophobically modified carboxymethylchitosan, and combinations thereof. In some embodiments, the branched polymer with a hydrophobic modification is hydrophobically modified cetyl hydroxyethylcellulose.

In some embodiments, the linear polypeptide or polysaccharide is selected from the group consisting of gellan gum, carrageenan, xanthan gum, biosaccharide gum-1, *sclerotium* gum, pectin, pullulan, guar gum, gum arabic, chondroitin, sulfate, alginic acid, sodium hyaluronate, hydrolyzed hyaluronic acid sodium polyglutamate, chitin, chitosan, starch, and combinations thereof. In some embodiments, the linear polypeptide or polysaccharide is sodium hyaluronate.

In some embodiments, the crosslinked polypeptide or polysaccharide, branched polymer with a hydrophobic modification; and linear polypeptide or polysaccharide comprise from about 0.01% to about 5% of the composition by weight.

In some embodiments, the moisturizing composition further comprises a mono-, or di-valent ion. In some embodiments, the mono-, or di-valent ion is selected from the group consisting of 2-Pyrrolidone-5-Carboxylic Acid and related salts, calcium PCA, sodium PCA, zinc PCA, magnesium PCA, sea salt, inorganic salts of citric acid, inorganic salts of lactic acid, calcium ascorbate, magnesium ascorbate, calcium oxide, calcium benzoate, calcium sorbate, calcium aspartate, magnesium carbonate, magnesium chloride, magnesium nitrate, and any combination thereof. In some embodiments, the mono-, or di-valent ion includes calcium PCA, magnesium PCA, and sea salt. Without wishing to be bound by theory, mono- and di-valent salts such as, but not limited to calcium PCA and Magnesium PCA can facilitate the cross-linking of a linear polypeptide or polysaccharide such as, but not limited to, gellan gum into an interpenetrating polymer network. In some embodiments, the mono-, or di-valent ion comprises between about 0.01% to about 5% of the composition by weight.

In some embodiments, the moisturizing compositions further comprises at least one humectant. In some embodiments, the at least one humectant is selected from the group consisting of glycerin, diglycerin, betaine, diols, propylene glycol, butylene glycol, pentylene glycol, propanediol, 1,2-hexanediol, D-ribose, glucose, sorbitol, dextrose, urea, 2-Pyrrolidone-5-Carboxylic Acid and related salts, sea salt, inorganic salts of citric acid, inorganic salts of lactic acid, ectoin, lactic acid, betaine, glycolic acid, lactobionic acid, and any combination thereof. In some embodiments, the humectant includes glycerin and pentylene glycol. In some embodiments, the humectant comprises at least about 30% of the composition by weight. In some embodiments, the humectant comprises between about 25% to about 80% of the composition by weight.

In some embodiments, the moisturizing composition further comprises an active agent. In some embodiments, the active agent is selected from the group consisting of glycerin, diglycerin, betaine, diols, propylene glycol, butylene glycol, pentylene glycol, propanediol, 1,2-hexanediol, D-ribose, glucose, sorbitol, dextrose, urea, 2-Pyrrolidone-5-Carboxylic Acid and related salts, sea salt, inorganic salts of citric acid, inorganic salts of lactic acid, ectoin, lactic acid, betaine, glycolic acid, lactobionic acid, and any combination thereof. In some embodiments, the active agent is a cell cycle modulator. In some embodiments, the cell cycle modulator is selected from the group consisting of phosphatidylglycerol, calcium PCA, Lysolecithin, and any combination thereof. Without wishing to be bound by theory, increasing moisture content at the skin's surface may not be enough as a long term strategy for combating the effects of dry skin. It is believed that the keratinocyte cell cycle has implications on dry skin. In biopsy studies, epidermal under-differentiation appears to be linked with dry skin in both young and old populations. In some embodiments, other cellular modulations can also be considered such as gene expression manipulation of AQP3 for improving skin hydration via cellular glycerol/water channels.

In some embodiments, the moisturizing composition further comprises a keratinocyte differentiation promoting agent. In some embodiments, the keratinocyte differentiation promoting agent is selected from the group consisting of phosphatidylglycerol, an organic salt of glycerophosphoinositol, calcium PCA, calcium lactate, calcium citrate or other forms of soluble calcium, hydroxyapatite, cortisone, ceramides, ergocalciferol, cholecalciferol, sphingolipids, and any combination thereof.

In some embodiments, the moisturizing compositions described herein may further comprise a preservative system. In some embodiments, the preservative system may comprise phenoxyethanol, capryl glycol, ethylhexylglycerin, hexylene glycol, sodium benzoate, potassium sorbate, methyl paraben, gluconolactone, lactic acid, sorbic acid, glyceryl caprylate, glyceryl undecylenate, ethanol, chlorphenesin, salicylic acid or any combination thereof. In some embodiments, the preservative system may comprise phenoxyethanol and capryl glycol and ethylhexylglycerin and hexylene glycol. In yet other embodiments, the preservative system may comprise glyceryl caprylate and glyceryl undecylenate.

In some embodiments, the moisturizing compositions described herein may further comprise caprylyl methicone-cosmetic silicone, PEG-12 dimethicone/PPG-20 Crosspolymer, alcohol denatured, isododecane, polysilicone-11, Dimethylacrylamide/Acrylic Acid/Polystyrene Ethyl Methacrylate Copolymer, coco-caprylate/Caprate, decyl glucoside, Hydroxyethyl Acrylate/Sodium Acryloyldimethyl Taurate Copolymer, Isohexadecane, and polysorbate 60.

The moisturizing compositions of the present invention may be formulated by those skilled in the art as liquids, solutions, emulsions, creams, lotions, suspensions, triturates, gels, jellies, foams, pastes, ointments, shampoos, adhesives and the like.

The moisturizing compositions of the present invention result in an improved capacity to absorb, attract, and bind water. The ability of a composition to absorb and retain water can be measured by Karl Fischer water content analysis and dynamic vapor sorption (DVS) analysis. In embodiments described herein, moisturizing compositions have greater than 25% water content as measured by Karl Fischer water content analysis. In embodiments described herein, moisturizing compositions have a weight gain between 10% and 100% from 5% to 95% relative humidity as measured by DVS.

The following paragraphs describe moisturizing compositions produced by the process described herein and it is understood that particular ingredients will fall under one of the categories comprising the interpenetrating polymer network.

In some embodiments, the moisturizing composition comprises Sodium Hyaluronate, Cetyl hydroxyethylcellulose, Gellan Gum, Glycerin, Pentylene Glycol, Magnesium PCA, Calcium PCA, and Sea Salt Fine.

In some embodiments, the moisturizing composition comprises DI Water, Glycerin, Phosphatidylglycerol, Pentylene Glycol, Bis-PEG-12 Dimethicone, Sodium Hyaluronate, *Pyrus Malus* (Apple) Fruit Extract, Phenoxyethanol, Capryl Glycol, Ethylhexylglycerin, Hexylene glycol, Calcium PCA, Gellan Gum, Magnesium PCA, Cetyl hydroxyethylcellulose, Sea Salt Fine, and Sodium benzoate.

In some embodiments, the moisturizing composition comprises DI Water, Glycerin, Pentylene Glycol, Bis-PEG-12 Dimethicone, Sodium Hyaluronate, Cetyl hydroxyethylcellulose, Adenosine, Magnesium PCA, Calcium PCA, Sodium benzoate, Sea Salt Fine, *Pyrus Malus* (Apple) Fruit Extract, Lactic acid, Kelcogel CG-HA Gellan Gum, Kelcogel CG-LA Gellan Gum, Phosphatidylglycerol, Ceteareth-25, Cetyl Alcohol, Behenic Acid, Cholesterol, Ceramide NP, Ceramide NS, Ceramide EOS, Ceramide EOP, Ceramide AP, Caprooyl Phytosphingosine, Caprooyl Sphingosine, Phenoxyethanol, Capryl Glycol, Ethylhexylglycerin, and Hexylene glycol.

In some embodiments, the moisturizing composition comprises DI Water, Caprylyl Methicone, PEG-12 Dimethicone, PPG-20 Crosspolymer, Alcohol Denatured, Sodium Hyaluronate, Cetyl hydroxyethylcellulose, Gellan Gum, Glycerin, Pentylene Glycol, Magnesium PCA, Calcium PCA, Sea Salt Fine, Glycerin, Isododecane, Dimethicone, Polysilicone-11, Butylene Glycol, Dimethylacrylamide, Acrylic Acid, Polystyrene Ethyl Methacrylate Copolymer, Coco-Caprylate, Caprate, Decyl Glucoside, Hydroxyethyl Acrylate, Sodium Acryloyldimethyl Taurate Copolymer, Isohexadecane, Polysorbate 60, Pentylene Glycol, Phenoxyethanol, Capryl Glycol, Ethylhexylglycerin, and Hexylene Glycol.

In some embodiments, the moisturizing composition comprises DI Water, Caprylyl Methicone, PEG-12 Dimethicone, PPG-20 Crosspolymer, Alcohol Denatured, Gellan Gum, *Pyrus Malus* (Apple) Fruit Extract, Adenosine, Magnesium PCA, Calcium PCA, Sodium benzoate, Sea Salt Fine, Phosphatidylglycerol, Ceteareth-25, Cetyl Alcohol, Behenic Acid, Cholesterol, Ceramide NP, Ceramide NS, Ceramide EOS, Ceramide EOP, Ceramide AP, Caprooyl Phytosphingosine, Caprooyl Sphingosine, Glycerin, Sodium Hyaluronate Crosspolymer, Cetyl hydroxyethylcellulose, Sodium Polyglutamate, Isododecane, Dimethicone, Polysilicone-11, Butylene Glycol, Dimethylacrylamide, Acrylic Acid, Polystyrene Ethyl Methacrylate Copolymer, Coco-Caprylate, Caprate, Decyl Glucoside, Hydroxyethyl Acrylate, Sodium Acryloyldimethyl Taurate Copolymer, Isohexadecane, Polysorbate 60, Pentylene Glycol, Phenoxyethanol, Capryl Glycol, Ethylhexylglycerin, and Hexylene Glycol.

In some embodiments, the IPN moisturizing composition is not a semi-interpenetrating polymer network. In some embodiments, the IPN moisturizing composition is not a sequential interpenetrating polymer network. In some embodiments, the IPN moisturizing composition is not a sequential semi-interpenetrating polymer network.

The moisturizing compositions of the present invention and/or for use in the methods of use, and/or methods of making embodied herein may be formulated for cosmetic and dermatological uses. In some embodiments, the moisturizing compositions of the present invention and/or for use in the methods of use, and/or methods of making embodied herein may be formulated for topical cosmetic and topical dermatological uses. In some embodiments, the compositions of the present invention and/or for use in the methods of use, and/or methods of making embodied herein may be formulated for topical administration. In some embodiments, the moisturizing compositions described herein may be formulated as creams, serums, milks, lotions, salves, oils, butters, gels, balms or any combination thereof.

In some embodiments, the moisturizing formulations described herein may be useful for promoting the exfoliation of dry skin, promoting the digestion of desmosomes, normalizing cell maturation, or any combination thereof.

In embodiments described herein, the method of treating dry skin comprises administering a moisturizing composition resulting in improvement in water retention and hydration of the skin.

In embodiments described herein, the method of treating dry skin comprises administering a moisturizing composition resulting in a self-adjusting moisture level unique to each individual.

In embodiments described herein, the method of treating dry skin comprises administering a moisturizing composition resulting in the improvement of the skin selected from the group consisting of radiance, fine lines, and overall dryness. Radiance is assessed as the reflection of light, e.g. shine. In embodiments described herein, the method of treating dry skin comprises administering a moisturizing composition resulting in diffuse reflectance and plumping of the skin.

In embodiments described herein, the method of treating dry skin comprises administering a moisturizing composition resulting in an improvement in the moisture content in the stratum corneum. In certain embodiments, the improvement in moisture content in the stratum corneum can be measured using 2 different techniques. The first technique uses the Corneometer to measure the capacitance of the surface of the skin, this technique allows for a measurement of the water content of the superficial epidermal layers down to a depth of about 0.1 mm. The second technique uses the SKICON to measure the conductance of the surface of the skin and the flow of electrons traveling down the surface of the skin.

In embodiments described herein, the method of treating dry skin comprises administering a moisturizing composition resulting in a decrease in the rate of transepidermal water loss (TEWL). TEWL can be measured using a Tewameter, the measurement is taken on the skin to assess passive water transport through the stratum corneum. The measurement of water evaporation is based on the diffusion principle in an open chamber, and the density gradient is measured indirectly by 2 pairs of sensors located inside the hollow cylinder probe. Data are analyzed by a microprocessor and reported in g/m2/h. A decrease in TEWL values reflects an improvement in the barrier properties of the skin and treatment of dry skin.

In embodiments described herein, the method of treating dry skin comprises administering a moisturizing composition resulting in the improvement of the viscoelastic properties of the skin selected from the group consisting of extensibility, resiliency, pure elasticity, biological elasticity and combinations thereof. In some embodiments, the viscoelastic properties can be measured using a Cutometer.

In embodiments described herein, the method of treating dry skin comprises administering a moisturizing composition resulting in the improvement of a subject's rating of skin attributes selected from the group consisting of moisturization, fine lines, radiance, suppleness, softness, smoothness, bouncy skin, dryness, overall appearance, overall comfort, tightness, firmness, plumpness, firmness, youthfulness and combinations thereof.

In some embodiments, the moisturizing formulations described herein may be useful for modulating keratinocyte function, normalizing keratinocyte differentiation, normalizing keratinocyte proliferation, modulating phosphatidylglycerol content of keratinocytes, or any combination thereof. Without wishing to be bound by theory, keratinocytes play a key role in the maintenance of healthy skin. The skin is the largest organ of the body and is composed of the epidermis and dermis. The most important function of the skin is to provide a physical and water permeability barrier. The epidermis is a continuously regenerating tissue, which differentiates to produce a mechanical and water permeability barrier. This barrier is established in the epidermis by a precisely regulated keratinocyte differentiation program that results in distinct epidermal layers. The structure of the epidermis is maintained by a finely tuned balance between keratinocyte proliferation and differentiation, which results in a multilayer structure consisting of basal, spinous, granular, and cornified layers. The innermost basal layer, which is in contact with the basement membrane, is composed of a single layer of undifferentiated keratinocytes with proliferative potential. The spinous layer consists of non-proliferating keratinocytes in an early differentiation stage with progressive maturation as the cells move from suprabasal layers outward. Spinous differentiation is followed by late differentiation in the granular layer and terminal differentiation in the outermost cornified layer. Once committed to differentiation, the cells in the basal layer lose their proliferative potential and move toward the terminally differentiated cornified layer. Precise regulation of differentiation in the epidermis is crucial for proper stratification and barrier formation to occur. Epidermal homeostasis is maintained in part by orchestrating the correct expression of genes in keratinocytes at each stage of differentiation. Alterations in this differentiation program can result in skin disorders, such as psoriasis, eczema, atopic dermatitis, skin cancers, such as squamous and basal cell carcinoma, and other conditions of the skin characterized by unregulated cell division. Thus, any upset in the balance of skin cell proliferation and differentiation signals can result in various disorders or other undesirable skin conditions. While an over-stimulation of keratinocyte proliferation may lead to hyperproliferative skin conditions, such as those mentioned above (i.e. psoriasis and various non-melanoma skin cancers), under-stimulation of keratinocyte proliferation may result in insufficient growth, such as that characterized by aging skin (skin cell senescence) or skin that has been damaged.

In some embodiments, the moisturizing compositions described herein may be useful for modulating and/or improving the moisture content of the skin, promoting the retention of long lasting hydration in the skin, increasing skin moisture, improving skin water balance, increasing skin hydration, decreasing transepidermal water loss, reducing evaporation of water from the skin, or any combination thereof. In some embodiments, the moisturizing compositions described herein may be useful for methods of treating and/or preventing dry and/or irritated skin. In some embodiments, the moisturizing compositions described herein may be useful for defending against, and reducing visible signs of aging for noticeably firmer, smoother, and flawless looking skin. In some embodiments, the moisturizing compositions described herein may be useful to erase the appearance of premature aging, including brown spots, dullness and discoloration. In some embodiments, the moisturizing compositions described herein may be useful to visibly brighten the skin. In some embodiments, the moisturizing compositions described herein may be useful to reduce the appearance of fine lines and wrinkles. In some embodiments, the moisturizing compositions described herein may be useful to creating a radiant complexion. In some embodiments, the moisturizing compositions described herein may be useful to shield the skin again biological and environmental aggressors associated with dry, irritated and sensitive skin. In some embodiments, the moisturizing compositions described herein may be useful to help the skin retain moisture and remain comfortable when challenged by climate and other environmental aggressors. In some embodiments, the moisturizing compositions described herein may be useful to rehydrate the skin. In some embodiments, the moisturizing compositions described herein may be useful to repair, renew, and/or enhance the skin's natural moisture barrier.

Embodiments, herein are directed to methods of promoting the exfoliation of dry skin, promoting the digestion of desmosomes, normalizing cell maturation, or any combination thereof, comprising administering a moisturizing composition comprising: an interpenetrating polymer network made up of a crosslinked polypeptide or polysaccharide; a branched polymer with a hydrophobic modification; and a linear polypeptide or polysaccharide. Embodiments herein are directed to methods of promoting the exfoliation of dry skin, promoting the digestion of desmosomes, normalizing cell maturation, or any combination thereof, comprising administering a moisturizing composition consisting essentially of: an interpenetrating polymer network made up of a crosslinked polypeptide or polysaccharide; a branched polymer with a hydrophobic modification; and a linear polypeptide or polysaccharide. Embodiments herein are directed to methods of promoting the exfoliation of dry skin, promoting the digestion of desmosomes, normalizing cell maturation, or any combination thereof, comprising administering a moisturizing composition consisting of: an interpenetrating polymer network made up of a crosslinked polypeptide or polysaccharide; a branched polymer with a hydrophobic modification; and a linear polypeptide or polysaccharide.

Embodiments, herein are directed to methods of modulating keratinocyte function, normalizing keratinocyte differentiation, normalizing keratinocyte proliferation, modulating phosphatidylglycerol content of keratinocytes, or any combination thereof, comprising administering a moisturizing composition comprising: an interpenetrating polymer network made up of a crosslinked polypeptide or polysaccharide; a branched polymer with a hydrophobic modification; and a linear polypeptide or polysaccharide. Embodiments herein are directed to methods of modulating keratinocyte function, normalizing keratinocyte differentiation, normalizing keratinocyte proliferation, modulating phosphatidylglycerol content of keratinocytes, or any combination thereof, comprising administering a moisturizing composition consisting essentially of: an interpenetrating polymer network made up of a crosslinked polypeptide or polysaccharide; a branched polymer with a hydrophobic modification; and a linear polypeptide or polysaccharide. Embodiments herein are directed to methods of modulating keratinocyte function, normalizing keratinocyte differentiation, normalizing keratinocyte proliferation, modulating phosphatidylglycerol content of keratinocytes, or any combination thereof, comprising administering a moisturizing composition consisting of: an interpenetrating polymer network made up of a crosslinked polypeptide or polysaccharide; a branched polymer with a hydrophobic modification; and a linear polypeptide or polysaccharide.

Embodiments, herein are directed to methods of modulating and/or improving the moisture content of the skin, promoting the retention of long lasting hydration in the skin, increasing skin moisture, improving skin water balance, increasing skin hydration, decreasing transepidermal water loss, reducing evaporation of water from the skin, shield the skin against biological and environmental aggressors associated with dry, irritated and sensitive skin, help the skin retain moisture and remain comfortable when challenged by climate and other environmental aggressors, or any combination thereof, comprising administering a moisturizing composition comprising: an interpenetrating polymer network made up of a crosslinked polypeptide or polysaccharide; a branched polymer with a hydrophobic modification; and a linear polypeptide or polysaccharide. Embodiments herein are directed to methods of modulating and/or improving the moisture content of the skin, promoting the retention of long lasting hydration in the skin, increasing skin moisture, improving skin water balance, increasing skin hydration, decreasing transepidermal water loss, reducing evaporation of water from the skin, shield the skin against biological and environmental aggressors associated with dry, irritated and sensitive skin, help the skin retain moisture and remain comfortable when challenged by climate and other environmental aggressors, or any combination thereof, comprising administering a moisturizing composition consisting essentially of: an interpenetrating polymer network made up of a crosslinked polypeptide or polysaccharide; a branched polymer with a hydrophobic modification; and a linear polypeptide or polysaccharide. Embodiments herein are directed to methods of modulating and/or improving the moisture content of the skin, promoting the retention of long lasting hydration in the skin, increasing skin moisture, improving skin water balance, increasing skin hydration, decreasing transepidermal water loss, reducing evaporation of water from the skin, shield the skin against biological and environmental aggressors associated with dry, irritated and sensitive skin, help the skin retain moisture and remain comfortable when challenged by climate and other environmental aggressors, or any combination thereof, comprising administering a moisturizing composition consisting of: an interpenetrating polymer network made up of a crosslinked polypeptide or polysaccharide; a branched polymer with a hydrophobic modification; and a linear polypeptide or polysaccharide.

Embodiments, herein are directed to methods of defending against, and reducing visible signs of aging for noticeably firmer, smoother, and flawless looking skin, erasing the appearance of premature aging, including brown spots, dullness and discoloration, visibly brightening the skin, reduce the appearance of fine lines and wrinkles, creating a radiant complexion, or any combination thereof, comprising administering a moisturizing composition consisting of: an interpenetrating polymer network made up of a crosslinked polypeptide or polysaccharide; a branched polymer with a hydrophobic modification; and a linear polypeptide or polysaccharide. Embodiments, herein are directed to methods of defending against, and reducing visible signs of aging for noticeably firmer, smoother, and flawless looking skin, erasing the appearance of premature aging, including brown spots, dullness and discoloration, visibly brightening the skin, reduce the appearance of fine lines and wrinkles, creating a radiant complexion, or any combination thereof, comprising administering a moisturizing composition consisting essentially of: an interpenetrating polymer network made up of a crosslinked polypeptide or polysaccharide; a branched polymer with a hydrophobic modification; and a linear polypeptide or polysaccharide. Embodiments herein are directed to methods of defending against, and reducing visible signs of aging for noticeably firmer, smoother, and flawless looking skin, erasing the appearance of premature aging, including brown spots, dullness and discoloration, visibly brightening the skin, reduce the appearance of fine lines and wrinkles, creating a radiant complexion, or any combination thereof, comprising administering a moisturizing composition comprising: an interpenetrating polymer network made up of a crosslinked polypeptide or polysaccharide; a branched polymer with a hydrophobic modification; and a linear polypeptide or polysaccharide. Embodiments herein are directed to methods of treating and/or preventing dry and/or irritated skin comprising administering a moisturizing composition comprising: an interpenetrating polymer network made up of a crosslinked polypeptide or polysaccharide; a branched polymer with a hydrophobic modification; and a linear polypeptide or polysaccharide. Embodiments herein are directed to methods of treating dry and/or irritated skin comprising administering a moisturizing composition consisting essentially of: an interpenetrating polymer network made up of a crosslinked polypeptide or polysaccharide; a branched polymer with a hydrophobic modification; and a linear polypeptide or polysaccharide. Embodiments herein are directed to methods of treating dry and/or irritated skin comprising administering a moisturizing composition consisting of: an interpenetrating polymer network made up of a crosslinked polypeptide or polysaccharide; a branched polymer with a hydrophobic modification; and a linear polypeptide or polysaccharide.

Embodiments herein are directed to a method for delivering an active ingredient or drug comprising administering an interpenetrating polymer network made up of a crosslinked polypeptide or polysaccharide; a branched polymer with a hydrophobic modification; a linear polypeptide or polysaccharide; and an active ingredient; wherein the crosslinked polypeptide or polysaccharide entraps the interlaced branched polymer with a hydrophobic modification, the linear polypeptide or polysaccharide, and the active ingredient or drug to form the interpenetrating polymer network. In some embodiments, the active ingredient or drug is selected from the group consisting of skin treatments, skin protectants, acne treatments, wrinkle treatments, exfoliating acids, skin brightening agents, and anti-inflammatory agents, In some embodiments, the acne treatment is selected from the group consisting of benzoyl peroxide, salicylic acid, willowbark extract, poly hydroxyacid, tannic acid, hydroxybenzoic acid, juniperic acid, tartaric acid, glycolic acid, lactic acid, and citric acid. In some embodiments, the wrinkle treatment is selected from the group consisting of retinol, antioxidants, vitamin A, retinoid, tretinoin, and tazarotene. In some embodiments, the anti-inflammatory agent is selected from the group consisting of ibuprofen, diclofenac, felbinac, ketoprofen, and piroxicam. In some embodiments, the skin protectant is glycerin. In some embodiments, the exfoliating acid is selected from the group consisting of glycolic acid, alpha hydroxyl acid (AHA), and polyhydroxyacid. In some embodiments, the skin brightening agent is selected from the group consisting of hydroquinone, hexyl resorcinol, and phenylethyl resorcinol.

In some embodiments, the compositions for use in the methods described herein are an interpenetrating polymer network comprising a crosslinked polypeptide or polysaccharide; a branched polymer with a hydrophobic modification; and a linear polypeptide or polysaccharide, wherein the crosslinked polypeptide or polysaccharide entraps the interlaced branched polymer with a hydrophobic modification and the linear polypeptide or polysaccharide to form the interpenetrating polymer network. In some embodiments, the polysaccharide capable of crosslinking, the branched polymer with a hydrophobic modification and the linear polypeptide or polysaccharide form an interpenetrating polymer network.

In some embodiments the crosslinked polypeptide or polysaccharide is selected from the group consisting of crosslinked gellan gum, crosslinked carrageenan, crosslinked chitosan crosslinked xanthan gum, sodium polyglutamate crosspolymer, polydextrose, and combinations thereof. In some embodiments, the crosslinked polypeptide or polysaccharide is crosslinked gellan gum.

In some embodiments the branched polymer with a hydrophobic modification is selected from the group consisting of hydrophobically modified hydroxypropylmethylcellulose, hydrophobically modified cetyl hydroxy propyl methyl cellulose, hydrophobically modified sodium acetyl hyaluronate, hydrophobically modified cetyl hydroxyethylcellulose, hydrophobically modified starch, hydrophobically modified carboxymethylchitosan, and combinations thereof.

In some embodiments, the branched polymer with a hydrophobic modification is hydrophobically modified cetyl hydroxyethylcellulose.

In some embodiments, the linear polypeptide or polysaccharide is selected from the group consisting of gellan gum, carrageenan, xanthan gum, biosaccharide gum-1, *sclerotium* gum, pectin, pullulan, guar gum, gum arabic, chondroitin, sulfate, alginic acid, sodium hyaluronate, hydrolyzed hyaluronic acid sodium polyglutamate, chitin, chitosan, starch, and combinations thereof. In some embodiments, the linear polypeptide or polysaccharide is sodium hyaluronate.

In some embodiments the crosslinked polypeptide or polysaccharide, branched polymer with a hydrophobic modification; and linear polypeptide or polysaccharide comprise from about 0.01% to about 5% of the composition by weight.

In some embodiments the moisturizing composition further comprises a mono-, or di-valent ion. In some embodiments the mono-, or di-valent ion is selected from the group consisting of 2-Pyrrolidone-5-Carboxylic Acid and related salts, calcium PCA, sodium PCA, zinc PCA, magnesium PCA, sea salt, inorganic salts of citric acid, inorganic salts of lactic acid, calcium ascorbate, magnesium ascorbate, calcium oxide, calcium benzoate, calcium sorbate, calcium aspartate, magnesium carbonate, magnesium chloride, magnesium nitrate, and any combination thereof. In some embodiments the mono-, or di-valent ion includes calcium PCA, magnesium PCA, and sea salt. Without wishing to be bound by theory, mono- and di-valent salts such as, but not limited to calcium PCA and Magnesium PCA can facilitate the cross-linking of a linear polypeptide or polysaccharide such as but not limited to gellan gum into an interpenetrating polymer network. In some embodiments, the mono-, or di-valent ion comprises between about 0.01% to about 5% of the composition by weight.

In some embodiments, the moisturizing composition further comprises at least one humectant. In some embodiments, the at least one skin conditioning/non polymeric humectant is selected from the group consisting of glycerin, diglycerin, betaine, diols, propylene glycol, butylene glycol, pentylene glycol, propanediol, 1,2-hexanediol, D-ribose, glucose, sorbitol, dextrose, urea, 2-Pyrrolidone-5-Carboxylic Acid and related salts, sea salt, inorganic salts of citric acid, inorganic salts of lactic acid, ectoin, lactic acid, betaine, glycolic acid, lactobionic acid, and any combination thereof. In some embodiments, the humectant includes glycerin and pentylene glycol. In some embodiments, the skin conditioning/non polymeric humectant comprises at least about 30% of the composition by weight. In some embodiments, the at least one humectant comprises between about 25% to about 80% of the composition by weight.

In some embodiments, the moisturizing composition further comprises an active agent. In some embodiments, the active agent is selected from the group consisting of glycerin, diglycerin, betaine, diols, propylene glycol, butylene glycol, pentylene glycol, propanediol, 1,2-hexanediol, D-ribose, glucose, sorbitol, dextrose, urea, 2-Pyrrolidone-5-Carboxylic Acid and related salts, sea salt, inorganic salts of citric acid, inorganic salts of lactic acid, ectoin, lactic acid, betaine, glycolic acid, lactobionic acid, and any combination thereof. In some embodiments, the active agent is a cell cycle modulator. In some embodiments, the cell cycle modulator is selected from the group consisting of phosphatidylglycerol, calcium PCA, Lysolecithin, and any combination thereof. Without wishing to be bound by theory, increasing moisture content at the skin's surface may not be enough as a long term strategy for combating the effects of dry skin. It is believed that the keratinocyte cell cycle has implications on dry skin. In biopsy studies, epidermal under-differentiation appears to be linked with dry skin in both young and old populations. In some embodiments, other cellular modulations can also be considered such as gene expression manipulation of AQP3 for improving skin hydration via cellular glycerol/water channels.

In some embodiments, the moisturizing composition further comprises a keratinocyte differentiation promoting agent. In some embodiments, the keratinocyte differentiation promoting agent is selected from the group consisting of phosphatidylglycerol, an organic salt of glycerophosphoinositol, calcium PCA, calcium lactate, calcium citrate or other forms of soluble calcium, hydroxyapatite, cortisone, ceramides, ergocalciferol, cholecalciferol, sphingolipids, and any combination thereof.

In some embodiments, the moisturizing compositions described herein may further comprise a preservative system. In some embodiments, the preservative system may comprise phenoxyethanol, capryl glycol, ethylhexylglycerin, hexylene glycol, sodium benzoate, potassium sorbate, methyl paraben, gluconolactone, lactic acid, sorbic acid, glyceryl caprylate, glyceryl undecylenate, ethanol, chlorphenesin, salicylic acid or any combination thereof. In some embodiments, the preservative system may comprise phenoxyethanol and capryl glycol and ethylhexylglycerin and hexylene glycol. In yet other embodiments, the preservative system may comprise glyceryl caprylate and glyceryl undecylenate.

In some embodiments, the moisturizing compositions described herein may further comprise caprylyl methicone-cosmetic silicone, PEG-12 dimethicone/PPG-20 Crosspolymer, alcohol denatured, isododecane, polysilicone-11, Dimethylacrylamide/Acrylic Acid/Polystyrene Ethyl Methacrylate Copolymer, coco-caprylate/Caprate, decyl glucoside, Hydroxyethyl Acrylate/Sodium Acryloyldimethyl Taurate Copolymer, Isohexadecane, and polysorbate 60.

Embodiments herein are directed to a method of producing a interpenetrating polymer network moisturizing composition, the method comprising: dispersing a non-crosslinked polypeptide or polysaccharide capable of crosslinking in water to form a first phase; combining a linear polypeptide or polysaccharide and a branched polymer with a hydrophobic modification with a humectant to form a second phase; combining the first and second phases to form a third phase of uncrosslinked interlaced polymers, polypeptides, or polysaccharides; adding a mono-valent ion, di-valent ion or a combination thereof to the third phase to crosslink one or more polypeptide, polymer, or polysaccharide to form an interpenetrating polymer network moisturizing composition. Without wishing to be bound by theory, combining the first phase with the second phase results in the formation of an interlaced polymer network but it is not until the addition of the crosslinking agent that the non-crosslinked polypeptide or polysaccharide capable of crosslinking actually becomes crosslinked to form an interpenetrating polymer network. This interpenetrating polymer network is made up of a crosslinked polypeptide or polysaccharide in a three dimensional structure; a branched polymer with a hydrophobic modification; and a linear polypeptide or polysaccharide, wherein the crosslinked polypeptide or polysaccharide entraps the interlaced branched polymer with a hydrophobic modification and the linear polypeptide or polysaccharide.

In some embodiments, the linear polypeptide or polysaccharide is a is selected from the group consisting of gellan gum, carrageenan, xanthan gum, biosaccharide gum-1, *sclerotium* gum, pectin, pullulan, guar gum, gum arabic, chondroitin, sulfate, alginic acid, sodium hyaluronate, hydrolyzed hyaluronic acid sodium polyglutamate, chitin, chitosan, starch, and combinations thereof.

In some embodiments, the non-crosslinked polypeptide or polysaccharide capable of crosslinking is selected from the group consisting of gellan gum, carrageenan, chitosan xanthan gum, sodium polyglutamate crosspolymer, polydextrose, and combinations thereof. In some embodiments, the non-crosslinked polypeptide or polysaccharide capable of crosslinking is gellan gum. In some embodiments, the gellan gum is selected from the group consisting of Kelcogel CG-HA, Kelcogel CG-LA, and any combination thereof. In some embodiments, the gellan gum comprises a mixture of Kelcogel CG-HA, and Kelcogel CG-LA. In some embodiments, dispersing the gellan gum in water to form a first phase further comprises pre-blending at least two gellan gum powders. In some embodiments, the at least two gellan gum powders are selected from the group consisting of Kelcogel CG-HA, Kelcogel CG-LA, and any combination thereof. Some embodiments further comprise heating the first phase to about 75° C. Some embodiments further comprise homogenizing the first phase.

In some embodiments, the first and second phases with at least one crosslinking agent in water to form the interpenetrating polymer network moisturizing composition further comprises the addition of USP Glycerin, *Pyrus Malus* (Apple) Fruit Extract, Glycerin, Pentylene Glycol, Bis-PEG-12 Dimethicone, Phenoxyethanol, capryl glycol, ethylhexylglycerin, hexylene glycol, or any combination thereof.

In some embodiments, the step of dispersing a non-crosslinked polypeptide or polysaccharide capable of crosslinking in water to form a first phase is heated to about 75° C. to about 90° C. In some embodiments, the non-crosslinked polypeptide or polysaccharide capable of crosslinking is a mixture of two different polypeptide or polysaccharide. In a preferred embodiment, the non-crosslinked polypeptide or polysaccharide capable of crosslinking is a mixture of Low Acyl (LA) gellan gum and High Acyl (HA) gellan gum. Without wishing to be bound by theory, the non-crosslinked polypeptide or polysaccharide capable of crosslinking unravels and becomes soluble with no organized structure once it is placed in water.

In some embodiments, the at least one crosslinking agent is selected from group consisting of 2-Pyrrolidone-5-Carboxylic Acid and related salts calcium PCA, sodium PCA, zinc PCA, magnesium PCA, sea salt, inorganic salts of citric acid, inorganic salts of lactic acid, calcium ascorbate, magnesium ascorbate, calcium oxide, calcium benzoate, calcium sorbate, calcium aspartate, magnesium carbonate, magnesium chloride, magnesium nitrate, and any combination thereof. In some embodiments, combining the first and second phases with at least one crosslinking agent in water to form the moisturizing composition further comprises adding adenosine, sodium benzoate, ESP sea salt fine or any combination thereof.

In some embodiments, the step of combining a linear polypeptide or polysaccharide and a branched polymer with a hydrophobic modification with a humectant to form a second phase further comprises dispersing pre-bended powdered ingredients into a pre-mixed mixture of liquid components to form the second phase, and heating the second phase to about 75° C. to about 80° C. In a preferred embodiment, the linear polypeptide is sodium hyaluronate and the branched polymer with a hydrophobic modification is hydrophobically modified hydroxyethylcellulose, each is combined and swell in the humectant, glycerin. The three components have no three dimensional structure and are heated to between 75° C. and 80° C.

In some embodiments, the step of combining the first and second phases to form a third phase of uncrosslinked interlaced polymers, polypeptides, or polysaccharides is accomplished by mixing the solutions to form a uniform thin liquid solution.

In some embodiments, the step of adding a mono-valent ion, di-valent ion or combination thereof to the third phase to crosslink one or more polypeptide, polymer, or polysaccharide further comprises cooling the mixture to about 22° C. to about 40° C. Without wishing to be bound by theory, the crosslinking of the polypeptide or polysaccharide capable of crosslinking begins to form a three dimensional structure immediately. This is visualized as a semi-solid continuous flowable gel. The crosslinking process continues until the solution has completely cooled to at least 40° C. The resulting 3 dimensional gel structure entraps the linear polypeptide or polysaccharide and a branched polymer with a hydrophobic modification in an uniform distribution as all the components started as fully miscible soluble components when heated to about 75° C.-80° C. The resulting composition is the interpenetrating polymer network described herein.

Some embodiments further comprise heating the interpenetrating polymer network moisturizing composition to between about 65° C. and about 80° C. Some embodiments, further comprise cooling the interpenetrating polymer network moisturizing composition to about 40° C. Some embodiments further comprise cooling the interpenetrating polymer network moisturizing composition to room temperature.

Some embodiments further comprise homogenizing the interpenetrating polymer network moisturizing composition until it is smooth and homogenous.

In some embodiments, combining the first and second phases with at least one crosslinking agent in water to form the interpenetrating polymer network moisturizing composition further comprises adding an active agent. In some embodiments, the active agent is selected from the group consisting of ceramide, water, humectants, natural moisturizing factors, osmolytes, bio-active hydrators Glycerin; Behenic Acid, Cholesterol, Ceramide NP, Ceramide NS, Ceramide EOS, Ceramide EOP, Ceramide AP, Caprooyl Phytosphingosine, Caprooyl Sphingosine, calcium salts, hydroxyapatite, palmitic acid, adenosine, peptides, and any combination thereof.

In some embodiments, combining the first and second phases with at least one crosslinking agent in water to form the interpenetrating polymer network moisturizing composition further comprises adding a keratinocyte differentiation promoting agent. In some embodiments, the keratinocyte differentiation promoting agent is selected from the group consisting of phosphatidylglycerol, an organic salt of glycerophosphoinositol, calcium PCA, calcium lactate, calcium citrate or other forms of soluble calcium, hydroxyapatite, cortisone, ceramides, ergocalciferol, cholecalciferol, sphingolipids, and any combination thereof.

In some embodiments, the humectant is selected from the group consisting lactic acid, glycerin, phosphatidylglycerol, ceteareth-25, glycerin, cetyl alcohol; behenic Acid, cholesterol, ceramide NP, ceramide NS, ceramide EOS, ceramide EOP, ceramide AP, caprooyl phytosphingosine, caprooyl sphingosine and any combination thereof.

In some embodiments, combining the first and second phases with at least one crosslinking agent in water to form the interpenetrating polymer network moisturizing composition further comprises adding further comprises a preservative system. In some embodiments, the preservative system may comprise phenoxyethanol, capryl glycol, ethylhexylglycerin, hexylene glycol, sodium benzoate, potassium sorbate, methyl paraben, gluconolactone, lactic acid, sorbic acid, glyceryl caprylate, glyceryl undecylenate, ethanol, chlorphenesin, salicylic acid or any combination thereof. In some embodiments, the preservative system may comprise phenoxyethanol and capryl glycol and ethylhexylglycerin and hexylene glycol. In yet other embodiments, the preservative system may comprise glyceryl caprylate and glyceryl undecylenate.

In some embodiments, the moisturizing compositions described herein may further comprise caprylyl methicone-cosmetic silicone, PEG-12 dimethicone/PPG-20 Crosspolymer, alcohol denatured, isododecane, polysilicone-11, Dimethylacrylamide/Acrylic Acid/Polystyrene Ethyl Methacrylate Copolymer, coco-caprylate/Caprate, decyl glucoside, Hydroxyethyl Acrylate/Sodium Acryloyldimethyl Taurate Copolymer, Isohexadecane, and polysorbate 60.

Some embodiments are directed to an interpenetrating polymer network moisturizing compositions formed by the methods described herein.

In some embodiments, the moisturizing compositions described herein may include a solvent. In some embodiments, the solvent is water.

Humectants for use in the compositions and methods described herein include, but are not limited to *pyrus malus* (apple) fruit extract, pentylene glycol, magnesium PCA ($Mg^{2+}$ crosslinks gellan gum; humectant natural moisturizing factor, balances calcium activity), calcium PCA ($Ca^{2+}$ crosslinks gellan gum; humectant natural moisturizing factor, calcium support differentiation), sea salt (humectant electrolyte breaks down thickener in Redefine creams), glycerin (humectant OTC skin protectant at 30%, supports desquamation via desmosome digestion), Phosphatidylglycerol (humectant carrier expresses AQ3, delivers glycerin into skin, differentiates keratinocytes), Bis-PEG-12 Dimethicone (sensory modifier with humectant properties) sodium benzoate (preservative with humectant properties), phenoxyethanol (and) capryl glycol (and) ethylhexylglycerin (and) hexylene glycol (preservatives with humectant properties), In some embodiments, agents that support and/or mimic the skin's natural barrier function and/or support differentiation can be used in the compositions and methods described herein. Such agents include, but are not limited to ceteareth-25, glycerin, cetyl alcohol, behenic acid, cholesterol, ceramide NP, ceramide NS, ceramide EOS, ceramide EOP, ceramide AP, caprooyl phytosphingosine, and caprooyl sphingosine.

In some embodiments, anti-aging and skin conditioning agents can be used in the compositions and methods described herein. Such agents include, but are not limited to adenosine In some embodiments, the moisturizing compositions described herein may include a moisturizer. In some embodiments, moisturizer include, but are not limited to lactic acid.

It is also known in the art that the active ingredients may be contained in such compositions with cosmetically and/or pharmaceutically acceptable diluents, fillers, disintegrants, binders, lubricants, surfactants, hydrophobic vehicles, water-soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

The cosmetic compositions described herein may be prepared, packaged, or sold in bulk as a single unit dose or as multiple unit doses and may be administered in the conventional manner by any route where they are active. For example, the compositions may be administered transdermally, subcutaneously, topically, and transdermal forms such as patches and creams. Specific modes of administration will depend on the indication. The selection of the specific route of administration and the dose regimen may be adjusted or titrated by the artisan according to known methods in order to obtain the optimal clinical response. All of the methods described herein may be carried out by administering the moisturizing compositions described herein by any such route for administration described herein. Additionally, the moisturizing compositions disclosed herein may be delivered by using any such route of administration for all of the dosage regimens described herein. The compositions and amounts of non-active ingredients in such a composition may depend on the amount of the active ingredient, and on the size and shape of the tablet or capsule. Such parameters may be readily appreciated and understood by one of skill in the art.

Embodiments of the invention are not limited to any particular agent encompassed by the classes of agents described above, and any agent that falls within any of these categories may be utilized in embodiments of the invention. Non-limiting examples of such agents are provided for clarity. Any of the secondary agents described above may be useful in embodiments of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

EXAMPLES

Example 1—Exemplary Interpenetrating Polymer Network Moisturizing Composition (3Dimensional 3Polymer Matrix—3D3P)

Table 1 provides the formulation for an exemplary 3D3P composition.

TABLE 1

| 3D3P formulation | | | |
|---|---|---|---|
| Trade name | Supplier | INCI | % W/W |
| | | DI Water/Aqua | 49.83 |
| Kelcogel CG-HA | Univar/Kelco CP | Gellan Gum | 0.03 |
| Kelcogel CG-LA | Univar/Kelco CP | Gellan Gum | 0.08 |
| USP Glycerin | | USP Glycerin | 27.00 |

TABLE 1-continued

3D3P formulation

| Trade name | Supplier | INCI | % W/W |
|---|---|---|---|
| Botanimoist AMS | Botanigenics | Pyrus Malus (Apple) Fruit Extract (and) Glycerin | 1.00 |
| Hydrolite 5 | Symrise | Pentylene Glycol | 3.00 |
| Gransil VX-419 | Grant Industries | Bis-PEG-12 Dimethicone | 3.00 |
| Botanistat PF64 | Botanigenics | Phenoxyethanol (and) capryl glycol (and) ethylhexylglycerin (and) hexylene glycol | 0.70 |
| Distinctive Bio Sodium Hyaluronate (#10094) | Resources of Nature | Sodium Hyaluronate | 0.12 |
| Polysurf 67CS | Ashland | Cetyl hydroxyethylcellulose | 0.30 |
|  |  | DI Water/Aqua | 10.00 |
| OriStar ADS | OriStar | Adenosine | 0.04 |
| Magnolidone | Solabia | Magnesium PCA | 0.30 |
| Calcidone | Solabia | Calcium PCA | 0.30 |
|  | OriStar | Sodium benzoate | 0.10 |
|  | Earth Supplied Products | ESP Sea Salt Fine | 0.10 |
| 90% lactic acid (dilute if needed) |  |  | 0.10 |
| Distinctive ® Bio-Signal Lipid RF-II (DC4038) | Resources of Nature | Glycerin (and) Phosphatidylglycerol | 3.00 |
| Skinmimics ® | Evonik | Ceteareth-25; Glycerin; Cetyl Alcohol; Behenic Acid; Cholesterol; Ceramide NP; Ceramide NS; Ceramide EOS; Ceramide EOP; Ceramide AP; Caprooyl Phytosphingosine; Caprooyl Sphingosine | 1.00 |
|  |  |  | 100.00 |

Example 2—Preparation of the Exemplary Interpenetrating Polymer Network Moisturizing Composition Table 2 provides instructions for preparing an exemplary 3D3P formulation.

TABLE 2

3D3P preparation

| Phase | Trade name | Supplier | INCI | % W/W |
|---|---|---|---|---|
| A |  |  | DI Water/Aqua | 49.83 |
| A | Kelcogel CG-HA | Univar/Kelco CP | Gellan Gum | 0.03 |
| A | Kelcogel CG-LA | Univar/Kelco CP | Gellan Gum | 0.08 |

Pre-blend powder, slowly disperse into water with propeller mixing, heat to 75 C. Start slow homogenizing at 75 C.. (to produce the First Phase)

| Phase | Trade name | Supplier | INCI | % W/W |
|---|---|---|---|---|
| B | USP Glycerin |  | USP Glycerin | 27.00 |
| B | Botanimoist AMS | Botanigenics | Pyrus Malus (Apple) Fruit Extract (and) Glycerin | 1.00 |
| B | Hydrolite 5 | Symrise | Pentylene Glycol | 3.00 |
| B | Gransil VX-419 | Grant Industries | Bis-PEG-12 Dimethicone | 3.00 |
| B | Botanistat PF64 | Botanigenics | Phenoxyethanol (and) capryl glycol (and) ethylhexylglycerin (and) hexylene glycol | 0.70 |
| B | Distinctive Bio Sodium Hyaluronate (#10094) | Resources of Nature | Sodium Hyaluronate | 0.12 |
| B | Polysurf 67CS | Ashland | Cetyl hydroxyethylcellulose | 0.30 |

Start mixing liquids with propeller, pre-blend powders and slowly disperse into liquid phase B. Heat to 75 C. under propeller agitation. (to produce the Second Phase)

| Phase | Trade name | Supplier | INCI | % W/W |
|---|---|---|---|---|
| C |  |  | DI Water/Aqua | 10.00 |
| C | OriStar ADS | OriStar | Adenosine | 0.04 |
| C | Magnolidone | Solabia | Magnesium PCA | 0.30 |
| C | Calcidone | Solabia | Calcium PCA | 0.30 |
| C |  | OriStar | Sodium benzoate | 0.10 |
| C |  | Earth Supplied Products | ESP Sea Salt Fine | 0.10 |

Disperse powders in water until fully dissolved, add heat if required.
Add B to A while under slow homogenization. (to produce the Third Phase) Continue homogenization for 10 minutes.
Add C to A/B while under slow homogenization. Allow to cool to 40 C. under slow homogenization.

| Phase | Trade name | Supplier | INCI | % W/W |
|---|---|---|---|---|
| D | 90% lactic acid (dilute if needed) |  |  | 0.10 |
| D | Distinctive ® Bio-Signal Lipid RF-II (DC4038) | Resources of Nature | Glycerin (and) Phosphatidylglycerol | 3.00 |

TABLE 2-continued

3D3P preparation

| Phase | Trade name | Supplier | INCI | % W/W |
|---|---|---|---|---|
| D | Skinmimics ® | Evonik | Ceteareth-25; Glycerin; Cetyl Alcohol; Behenic Acid; Cholesterol; Ceramide NP; Ceramide NS; Ceramide EOS; Ceramide EOP; Ceramide AP; Caprooyl Phytosphingosine; Caprooyl Sphingosine | 1.00 |

Add D to A/B/C under slow homogenization allow to cool to RT. Homogenize until product is smooth and consistent.

100.00
pH at RT: 4.44

Example 3-3D-3P Interpenetrating Polymer Network Hydration Scaffold (Dilutable Concentrate)

Below is an example of a 3D-3P Interpenetrating Polymer_Network Hydration Scaffold (dilutable concentrate) formed using Sodium Hyaluronate Crosspolymer, Table 3. The product had a clear homogenous gel with viscoelastic properties. This example likely formed a semi-interpenetrating polymer network. It is likely that all polymers are miscible in solution and form a continuous phase but nothing exists to hold them in place since Sodium Hyaluronate Crosspolymer was already crosslinked prior to mixing the polymers in solution. In comparison 3D3P Interpenetrating Polymer_Network from Example 1 cross-links the gellan gum (with calcium and magnesium) after the polymers have interlaced in solution. This cross linking secures a more rigid structure trapping the polymers together.

TABLE 3

3D-3P Interpenetrating Polymer_Network Hydration Scaffold

| Raw Material | INCI | % W/W |
|---|---|---|
| Glycerin | Glycerin | 66.50 |
| Hylasome EG6 | Sodium Hyaluronate Crosspolymer (and) pentylene glycol and ethylhexylglycerin | 30.00 |
| Natrosol 330CS | Cetyl hydroxyethylcellulose | 2.50 |
| Tego Cosmo PGA | Sodium Polyglutamate | 1.00 |
|  |  | 100.00 |

A 3D3P (3 dimensional 3 polymer) interpenetrating polymer network (IPN) was assembled by unraveling dry spooled gellan gum in water and introducing a hydrophobically modified cellulose and a linear sodium hyaluronate into the gellan gum solution. Once the 3 polymers were interlaced divalent magnesium and calcium ions were added in the form of natural moisturizing factors (PCA salts) to cross-link the gellan gum forming a gelatinous IPN. The composition contained a blend of humectants including about 30% glycerin to attract and bind water in addition to potentially assisting in normalizing desquamation. The introduction of calcium ions in the form a pyroglutamic acid salt also had the potential to support barrier homeostasis. This superhumectant 3D3P IPN (represented in FIG. 16B) was examined with both in vitro and in vivo techniques to determine the effectiveness in restoring hydration levels at the stratum corneum and the capacity of this IPN to attract and bind water molecules.

Example 4—Exemplary Interpenetrating Polymer Network Moisturizing Composition Formulated for Use as a Body Milk The interpenetrating polymer network moisturizing compositions described herein (i.e. 3D3P Moisture Essence) can be formulated for use in a body milk, Table 4.

TABLE 4

3D3P Moisture Essence in a body milk formulation

| Phase | Trade name | Supplier | INCI | % W/W |
|---|---|---|---|---|
| A | USP Glycerin |  | USP Glycerin | 5.00 |
| A | Barsolv NS-100 | Barnet | Polyglyceryl-10 Laurate | 2.4 |
| Slowly disperse Glycerin into Barsolv NS-100 with propeller mixing until a homogeneous gel is obtained |
| B | Hydrasynol DOI | Sytheon | Isosorbide dicaprylate | 2.00 |
| B | Lipex Shealight | AAK | Shea Butter Ethyl Esters | 5.00 |
| B | VOLASIL ® DM-2 | Chemtec | Dimethicone | 1.00 |
| B | Barsil 2001 | Barnet | Dimethicone | 0.30 |
| Start mixing liquids with propeller, and slowly disperse into gel phase A. |
| C | 3D3P Moisture Essence | RF | Proprietary Blend*RF 3D3P Moisture Essence Ingredient Deck | 10.00 |

TABLE 4-continued

3D3P Moisture Essence in a body milk formulation

| Phase | Trade name | Supplier | INCI | % W/W |
|---|---|---|---|---|
| C | Butylene Glycol | | Butylene Glycol | 3.50 |
| C | | | DI Water/Aqua | 64.60 |
| C | Dow Corning ® EP 9801 Hydro Cosmetic Powder | Dow Corning/Nexeo Sol | Dimethicone/Vinyl Dimethicone Crosspolymer (and) Silica (and) Butylene Glycol | 3.00 |
| C | SIMULGEL ™ INS 100 | Seppic | Hydroxyethyl Acrylate/Sodium Acryloyldimethyl Taurate Copolymer (and) Isohexadecane (and) Polysorbate 60 | 2.50 |
| C | Botanistat PF64 | Botanigenics | Phenoxyethanol (and) capryl glycol (and) ethylhexylglycerin (and) hexylene glycol | 0.70 |

Start mixing liquids with propeller, and slowly add Simulgel INS 100 mixing until a homogeneous gel is obtained. Disperse into gel phase (A&B) and mixing well.

Example 5—Exemplary Interpenetrating Polymer Network Moisturizing Composition for Use as a Body Serum The interpenetrating polymer network moisturizing compositions described herein (i.e. 3D3P Moisture Essence) can be formulated for use in a body serum, Table 5.

TABLE 5

3D3P Moisture Essence in a body serum formulation

| Phase | Trade name | Supplier | INCI | % W/W |
|---|---|---|---|---|
| A | | | DI Water/Aqua | 30 |
| A | Dow Corning EL-7040 | Dow Corning/Nexeo Solutions | Caprylyl Methicone (and) PEG-12 Dimethicone/PPG-20 Crosspolymer | 15.00 |

Slowly disperse into water with propeller mixing until a homogeneous gel is obtained

| | | | | |
|---|---|---|---|---|
| B | USP Glycerin | | USP Glycerin | 10.00 |
| B | 3D3P Moisture Essence | RF | Proprietary Blend*RF 3D3P Moisture Essence Ingredient Deck | 10.00 |
| B | SD Alcohol 40B | | Alcohol Denatured | 10.00 |
| B | | | DI Water/Aqua | 24.50 |
| B | Botanistat PF64 | Botanigenics | Phenoxyethanol (and) capryl glycol (and) ethylhexylglycerin (and) hexylene glycol | 0.50 |

Start mixing liquids with propeller, and slowly disperse into gel phase A.

Example 6—Exemplary Interpenetrating Polymer Network Moisturizing Composition for Use as an Eye Cream The interpenetrating polymer network moisturizing compositions described herein (i.e. 3D3P Moisture Essence) can be formulated for use in an eye cream, Table 6.

TABLE 6

3D3P Moisture Essence as an eye cream formulation

| Phase | Trade name | Supplier | INCI | % W/W |
|---|---|---|---|---|
| A | 3D3P Moisture Essence | RF | Proprietary Blend*RF 3D3P Moisture Essence Ingredient Deck | 15.00 |
| A | Dow Corning EL-7040 | Dow Corning/Nexeo Solutions | Caprylyl Methicone (and) PEG-12 Dimethicone/PPG-20 Crosspolymer | 20.00 |

Slowly disperse 3D3P Blend into DC EL-7040 with propeller mixing until a homogeneous gel is obtained.

| | | | | |
|---|---|---|---|---|
| B | | | DI Water/Aqua | 61.20 |
| B | SD Alcohol 40B | | Alcohol Denatured | 2.00 |
| | Botanistat PF64 | Botanigenics | Phenoxyethanol (and) capryl glycol (and) ethylhexylglycerin (and) hexylene glycol | 0.80 |

TABLE 6-continued

3D3P Moisture Essence as an eye cream formulation

| Phase | Trade name | Supplier | INCI | % W/W |
|---|---|---|---|---|
| B | Sepiplus 265 | Seppic | Polyacrylate-13 (and) Polyisobutene (and) Polysorbate 20 | 1.00 |

Start mixing liquids with propeller, and slowly disperse into gel phase A.

Example 7-Exemplary Interpenetrating Polymer Network Moisturizing Composition for Use as an Eye Cream The interpenetrating polymer network moisturizing compositions described herein (i.e. 3D3P Moisture Essence) can be formulated for use in an eye cream, Table 7.

TABLE 7

3D3P Eye Cream (30% 3D3P Peach)

| Trade Name | Supplier | INCI Components | Phase | % w/w | To Add (g) |
|---|---|---|---|---|---|
| 3D3P Moisture Essence | Rodan and Fields Proprietary | (formulation described above) | A | 30.00 | 360.00 |
| Dow Corning EL-7040 | Dow Corning | Caprylyl Methicone | | 16.00 | 240.00 |
| | | PEG-12 Dimethicone/PPG-20 Crosspolymer | | 4.00 | |
| Gransil SiW-050 IS | Grant Industries | Isododecane | | 0.48 | 12.00 |
| | | Water | | 0.21 | |
| | | Dimethicone | | 0.11 | |
| | | Polysilicone-11 | | 0.10 | |
| | | Butylene Glycol | | 0.04 | |
| | | Dimethylacrylamide/Acrylic Acid/Polystyrene Ethyl Methacrylate Copolymer | | 0.03 | |
| | | Coco-Caprylate/Caprate | | 0.025 | |
| | | Caprylyl Glycol | | 0.001 | |
| | | Phenoxyethanol | | 0.001 | |
| | | Hexylene Glycol | | 0.001 | |
| | | Decyl Glucoside | | 0.002 | |
| Deionized Water | Lab Supply | Water | B | 34.75 | 417.00 |
| Symsave H | Symrise | Hydroxyacetophenone | | 0.50 | 6.00 |
| Dow Corning PF-9510 Elastomer | Dow Corning | Dimethicone/Vinyl Dimethicone Crosspolymer | | 0.4238 | 9.00 |
| | | Water | | 0.30 | |
| | | C12-14 Pareth-12 | | 0.0188 | |
| | | Phenoxyethanol | | 0.0056 | |
| | | Chlorophenesin | | 0.0019 | |
| Chlorellagen DP | Barnet Products Corp. | Water | | 0.975 | 12.00 |
| | | Chlorella vulgaris extract | | 0.025 | |
| CurePassion | Ichimaru Pharcos | Water | | 1.38 | 24.00 |
| | | Butylene Glycol | | 0.60 | |
| | | Passiflora Edulis Fruit Extract | | 0.02 | |
| Sepiplus 265 | Seppic, Inc. | Acrylamide/Ammonium Acrylate Copolymer | C | 0.96 | 19.20 |
| | | Polyisobutene | | 0.448 | |
| | | Polysorbate 20 | | 0.08 | |
| | | Water | | 0.048 | |
| | | Sorbitan Isostearate | | 0.064 | |
| Dow Corning 9576 Smooth Away | Dow Corning | Dimethicone | | 3.1875 | 45.00 |
| | | Dimethicone/Vinyl Dimethicone Crosspolymer | | 0.1313 | |
| | | Dimethicone Crosspolymer | | 0.2813 | |
| | | Beeswax | | 0.1313 | |
| | | Silica | | 0.0094 | |
| | | Silica Silylate | | 0.0094 | |
| ICP Dragon Fruit Extract | Devreaux Specialties | Hylocereus Undatus Fruit Extract | | 0.99 | 12.00 |
| | | Phenoxyethanol | | 0.008 | |
| | | Sodium Metabisulfite | | 0.002 | |
| Caffeine | Ampak Co., Inc. | Caffeine | | 1.00 | 12.00 |
| SD 40B Alcohol | Lab Supply | SD 40B Alcohol | | 2.00 | 24.00 |

TABLE 7-continued

3D3P Eye Cream (30% 3D3P Peach)

| Trade Name | Supplier | INCI Components | Phase | % w/w | To Add (g) |
|---|---|---|---|---|---|
| Sangelose 60L | Ikedia Corp. of America | Hydroxypropyl Methylcellulose Stearoxy Ether | D | 0.25 | 3.00 |
| Timiron Synwhite 40 | EMD Performance Materials | Fluorphlogopite Titanium Dioxide Tin Oxide | | 0.1152 0.0432 0.0016 | 1.92 |
| FAS70USI White | DD Chemco | Titanium Dioxide Cyclopentasiloxane PEG/PPG 18/18 Dimethicone Triethoxycaprylylsilane | | 0.0891 0.0325 0.0065 0.002 | 1.56 |
| FAS50EYSI Yellow | DD Chemco | Iron Oxides (CI 77492) Cyclopentasiloxane PEG/PPG 18/18 Dimethicone Triethoxycaprylylsilane | | 0.049 0.0338 0.0163 0.001 | 1.20 |
| FAS55ERSI Red | DD Chemco | Iron Oxides (Cl 77491) Cyclopentasiloxane PEG/PPG 18/18 Dimethicone Triethoxycaprylylsilane | | 0.0049 0.0034 0.0016 0.0001 | 0.12 |

Processing Instructions: 1.) Add phase A items to main vessel. Mix vigorously until a gel is formed. 2.) Premix phase B items. Heat to 40° C. and mix until uniform. 3.) Slowly add phase B to phase A with moderate mixing. Mix until smooth and uniform. 4.) Add phase C items one at a time, mixing between additions. Mix until smooth. 5.) Add phase D items to match color standard (Pantone 155C). Homogenize until smooth.

Example 8—Exemplary Interpenetrating Polymer Network Moisturizing Composition for Use as an Eye Serum The interpenetrating polymer network moisturizing compositions described herein (i.e. 3D3P Moisture Essence) can be formulated for use in an eye serum, Table 8.

TABLE 8

3D3P Moisture Essence in an eye serum formulation

| Phase | Trade name | Supplier | INCI | % W/W |
|---|---|---|---|---|
| A | 3D3P Moisture Essence | RF | Proprietary Blend*RF 3D3P Moisture Essence Ingredient Deck | 38.5 |
| A | Dow Corning EL-7040 | Dow Corning/Nexeo Solutions | Caprylyl Methicone (and) PEG-12 Dimethicone/PPG-20 Crosspolymer | 53.50 |
| Slowly disperse 3D3P Blend into DC EL-7040 with propeller mixing until a homogeneous gel is obtained. | | | | |
| B | ACQUACELL | Barnet | Water & Glycerin & *Citrullus vulgaris* (Watermelon) Fruit Extract & *Pyrus malus* (Apple) Fruit Extract & *Lens Esculenta* (Lentil) Fruit Extract & Sodium PCA & Sodium Lactate | 4.00 |
| B | SymGlucan | Symrise | Aqua, Glycerin, Beta-Glucan | 4.00 |
| Start mixing liquids with propeller, and slowly disperse into gel phase A. | | | | |

Example 9: Exemplary Interpenetrating Polymer Network Composition for Use as a Teen Acne Wash The interpenetrating polymer network moisturizing compositions described herein (i.e. 3D3P Moisture Essence) can be formulated for use in a teen acne wash, Table 9.

TABLE 9

Teen Acne Wash

| Trade Name | Supplier | INCI Components | Phase | % w/w | To Add (g) |
| --- | --- | --- | --- | --- | --- |
| 3D3P Moisture Essence | Rodan and Fields Proprietary | (formulation described above) | A | 15.00 | 120.00 |
| Diglycerin S | Rossow | Diglycerin | | 3.00 | 24.00 |
| Barsolve NS-100 | Barnet Products Corp. | Polyglyceryl-10 Laurate | | 3.00 | 24.00 |
| GT-730 | Adeka Corp. | PEG-240/HDI Copolymer Bis-Decyltetradeceth-20 Ether | | 0.07 | 8.00 |
| | | Butylene Glycol | | 0.12 | |
| | | Water | | 0.80 | |
| | | Potassium Laurate | | 0.0075 | |
| | | Tocpherol | | 0.0025 | |
| Iselux Ultra Mild | Chem Tech | Water | | 6.54 | 80.00 |
| | | Sodium Lauroyl Methyl Isethionate | | 1.20 | |
| | | Cocamidopropyl Betaine | | 0.90 | |
| | | Sodium Methyl Oleoyl Taurate | | 0.70 | |
| | | Lauryl Glucoside | | 0.30 | |
| | | Coco-Glucoside | | 0.30 | |
| | | Sodium Benzoate | | 0.06 | |
| Citric Acid Granular | Spectrum Chemical Mfg. Corp. | Citric Acid | | 1.00 | 8.00 |
| GlycoFilm 1.5P | Solabia | Water | | 2.919 | 24.00 |
| | | Biosaccharide Gum 4 | | 0.036 | |
| | | Phenoxyethanol | | 0.045 | |
| Lipacide C8G | Seppic, Inc. | Capryloyl Glycine | | 0.50 | 4.00 |
| Stearic Acid | AE Chemie, Inc. | Stearic Acid | | 3.00 | 24.00 |
| Amilite GCS-11 | Ajinomoto | Sodium Cocoyl Glycinate | B | 20.00 | 160.00 |
| Glycerin | Jeen Chemical, Inc. | Glycerin | | 7.00 | 56.00 |
| AmisafeLL-DS-22 | Ajinomoto | Disodium Sebacoyl Bis-Lauramidolysine | | 0.05 | 4.00 |
| | | Water | | 0.45 | |
| Deionized Water | Lab Supply | Water | | 19.30 | 154.40 |
| Symsave H | Symrise | Hydroxyacetophenone | | 0.50 | 4.00 |
| Curoxyl 42 | Vantage | Benzoyl Peroxide | C | 5.00 | 100.00 |
| | | Water | | 7.50 | |
| Sepimat HBV | Seppic, Inc. | Methyl Methacrylate Crosspolymer | | 0.50 | 4.00 |
| Menthol | Ampak, Co. | Menthol | | 0.20 | 1.60 |

Mixing Instructions: 1.) Mix phase A and heat to 65° C. 2.) At 65° C., add Phase B ingredients, one at a time, mixing between additions. Continue mixing until smooth and uniform. 3.) Begin cooling to 30° C. with slow mixing. At 30° C., add phase C ingredients one at a time, mixing between additions. Mix until smooth and uniform.

Example 10—Dynamic Vapour Sorption (DVS) Testing

One sample of glycerin (1505-56) and three polysaccharide in glycerin samples (1505-57, 1505-58, and 1505-59) were tested using the dynamic vapor sorption (DVS) analyses. The formulation for each is provided in Table 10.

TABLE 10

Test sample formulations

| Trade name | Supplier | INCI | 1505-56 % W/W | 1505-57 % W/W | 1505-58 % W/W | 1505-59 (AKA 1505-21 or 3D3P Moisture Essence) % W/W |
|---|---|---|---|---|---|---|
| | | DI Water/Aqua | 0 | 0 | 49.83 | 49.83 |
| Kelcogel CG-HA | Univar/Kelco CP | Gellan Gum | 0 | 0 | 0.03 | 0.03 |
| Kelcogel CG-LA | Univar/Kelco CP | Gellan Gum | 0 | 0 | 0.08 | 0.08 |
| USP Glycerin | | USP Glycerin | 100.00 | 99.00 | 27.00 | 27.00 |
| Botanimoist AMS | Botanigenics | *Pyrus Malus* (Apple) Fruit Extract (and) Glycerin | 0 | 0 | 0 | 1.00 |
| Hydrolite 5 | Symrise | Pentylene Glycol | 0 | 0 | 0 | 3.00 |
| Gransil VX-419 | Grant Industries | Bis-PEG-12 Dimethicone | 0 | 0 | 0 | 3.00 |
| Botanistat PF64 | Botanigenics | Phenoxyethanol (and) capryl glycol (and) ethylhexylglycerin (and) hexylene glycol | 0 | 0 | 0 | 0.70 |
| Distinctive Bio Sodium Hyaluronate (#10094) | Resources of Nature | Sodium Hyaluronate | 0 | 1.30 | 0.12 | 0.12 |
| Polysurf 67CS | Ashland | Cetyl hydroxyethylcellulose | 0 | 0 | 0.30 | 0.30 |
| | | DI Water/Aqua | 0 | 0 | 10.00 | 10.00 |
| OriStar ADS | OriStar | Adenosine | 0 | 0 | 0 | 0.04 |
| Magnolidone | Solabia | Magnesium PCA | 0 | 0 | 0.30 | 0.30 |
| Calcidone | Solabia | Calcium PCA | 0 | 0 | 0.30 | 0.30 |
| | OriStar | Sodium benzoate | 0 | 0.10 | 0 | 0.10 |
| | Earth Supplied Products | ESP Sea Salt Fine | 0 | 0 | 0 | 0.10 |
| 90% lactic acid (dilute if needed) | | | 0 | 0 | 0 | 0.10 |
| Distinctive ® Bio-Signal Lipid RF-II (DC4038) | Resources of Nature | Glycerin (and) Phosphatidylglycerol | 0 | 0 | 0 | 3.00 |
| Skinmimics ® | Evonik | Ceteareth-25; Glycerin; Cetyl Alcohol; Behenic Acid; Cholesterol; Ceramide NP; Ceramide NS; Ceramide EOS; Ceramide EOP; Ceramide AP; Caprooyl Phytosphingosine; Caprooyl Sphingosine | 0 | 0 | 0 | 1.00 |
| | | | | | | 100.00 |

Results and Discussion: It was determined that glycerin lot RF 1505-56 and polysaccharide in glycerin lots RF 1505-58 and RF 1505-59 were able to be directly introduced into the titration vessel given their solubility in the methanol-based solvent. Polysaccharide in glycerin lot RF 1505-57 was not soluble in the methanol-based solvent or other common solvent combinations and had to be analyzed using the oven.

The samples be dried in an oven at 105° C. for four hours prior to analysis of the samples. The water content values for the individual replicates for each of the samples as well as the average water content are reported in Table 11.

TABLE 11

Water Content results

| Sample No. | Method | Replicate No. | Amount (g) | Water Content (%) | Average Water Content (%) |
|---|---|---|---|---|---|
| 1505-56 | Wet | 1 | 0.3791 | 1.51 | 1.49 |
| | | 2 | 0.2950 | 1.48 | |
| | | 3 | 0.4189 | 1.49 | |
| 1505-57 | Oven | | 0.5750 | 1.80 | 1.80 |
| 1505-58 | Wet | 1 | 0.0371 | 45.11 | 45.37 |
| | | 2 | 0.0401 | 45.25 | |
| | | 3 | 0.0544 | 45.75 | |

TABLE 11-continued

Water Content results

| Sample No. | Method | Replicate No. | Amount (g) | Water Content (%) | Average Water Content (%) |
|---|---|---|---|---|---|
| 1505-59 | Wet | 1 | 0.0660 | 31.82 | 31.75 |
| | | 2 | 0.0567 | 31.82 | |
| | | 3 | 0.0407 | 31.61 | |

Dynamic vapour sorption (DVS) is a technique that measures the uptake and loss of moisture of a material by passing a carrier gas of known humidity over a sample contained in a weighing mechanism. The weight versus time curves for the DVS data from the four samples are presented in FIGS. 1, 3, 5, and 7 while the percent weight change versus percent relative humidity (RH) curves are presented in FIGS. 2, 4, 6, and 8, respectively. The DVS results are summarized in Table 12.

TABLE 12

Summary of DVS Results

| Samples | Sorption/Desorption* |
|---|---|
| 1505-56 | 0.07% loss upon drying at 5% RH |
| | 36.93% gain from 5 to 95% RH |
| | 7.42% gain from 95% to 75% RH |
| | 33.92% loss from 75 to 5% RH |
| 1505-57 | 0.15% loss upon drying at 5% RH |
| | 53.82% gain from 5 to 95% RH |
| | 7.51% gain from 95% to 75% RH |
| | 52.12% loss from 75 to 5% RH |
| 1505-58 | 22.12% loss upon drying at 5% RH |
| | 11.33% loss from 5 to 35% RH |
| | 28.27% gain from 35% to 95% RH |
| | 3.66% gain from 95 to 85% RH |
| | 36.41% loss from 85 to 5% RH |
| 1505-59 | 18.11% loss upon drying at 5% RH |
| | 3.11% gain from 5 to 15% RH |
| | 106.56% gain from 15% to 95% RH |
| | 11.95% gain from 95 to 85% RH |
| | 107.92% loss from 85 to 5% RH |

*RH = relative humidity; All percent weight change values are calculated with respect to the initial starting weight.

Conclusions: The KF results showed that the glycerin lot RF 1505-56 and polysaccharide in glycerin lot RF 1505-57 had similar water contents below 2% after drying. Polysaccharide in glycerin lots RF 1505-58 and RF 1505-59 had significantly higher water contents than the other two samples with lot RF 1505-58 showing the highest water content after drying.

Example 11—A Single Center, Double-Blind Clinical Trial Assessing the Efficacy of Hydrating Essences when Used by Women with Photodamaged Facial Skin Photodamaged/aged facial skin is characterized by a dull appearance and the presence of fine lines, wrinkles, and mottled pigmentation, among other changes that contribute to visual signs of aging. Fine lines and wrinkles arise due to the breakdown of collagen, while decreases in the amount of water held in the epidermis result in the accentuation of fine lines as well as visible and tactile skin roughness.

This single-center, double-blind clinical trial was conducted over the course of 8 days to assess the efficacy of the Sponsor's hydrating essence when used by women with mild to moderate dry skin, global fine lines, and skin dullness on the face. A total of 39 subjects completed study participation in 1 of the following treatment cells: Cell 1 (14 subjects): Formulation 1505-21 (Table 10), Cell 2 (13 subjects): Formulation 1505-42B (Table 13), Cell 3 (12 subjects): Formulation benchmark/Amore Pacific.

TABLE 13

Formulation 1505-42B

| INCI | CAS # | % w/w |
|---|---|---|
| DI Water/Aqua | 7732-18-5 | 54.50% |
| Caprylyl Methicone | 17955-88-3 | 12.50% |
| PEG-12 Dimethicone/PPG-20 Crosspolymer | 1310362-62-9 | |
| Alcohol Denatured | 64-17-5 | 10.00% |
| Proprietary Blend*RF 3D3P Moisture Essence Ingredient Deck (see Table 2 and 3) | | 10.00% |
| Glycerin | 56-81-5 | 8.00% |
| Isododecane | 13475-82-6 | 1.00% |
| Dimethicone | 9006-65-9, 63148-62-9 | |
| Polysilicone-11 | 63394-02-5 | |
| Butylene Glycol | 107-88-0 | |
| Dimethylacrylamide/Acrylic Acid/Polystyrene Ethyl Methacrylate Copolymer | 547763-79-1 | |
| Coco-Caprylate/Caprate | 95912-86-0 | |
| Decyl Glucoside | 58846-77-8 | |
| Hydroxyethyl Acrylate/Sodium Acryloyldimethyl Taurate Copolymer | 111286-86-3 | 2.10% |
| Isohexadecane | 63793-60-2 | |
| Polysorbate 60 | 9005-67-8 | |
| Pentylene Glycol | 5343-92-0 | 1.50% |
| Phenoxyethanol | 122-99-6 | 0.40% |
| Capryl Glycol | 1117-86-8 | |
| Ethylhexylglycerin | 70445-33-9 | |
| Hexylene Glycol | 107-41-5 | |

During the course of the study, subjects applied the assigned test material to the entire face every evening after cleansing and toning, as directed. Subjects also performed an in-clinic application on day 1 and day 8. Clinical evaluations were conducted at visit 1 (baseline [pre-application] and 30 minutes post-application), visit 2 (8 hours post-application), and visit 3 (day 8: pre-application and 30 minutes post-application). See Table 14 for Study outline.

TABLE 14

Study Outline

| Procedures | Day 1 (BL) | Day 1 30 mins PA | Day 1 8 hrs PA | Days 2-7 | Day 8 (pre-application) | Day 8 | Day 8 30 mins PA |
|---|---|---|---|---|---|---|---|
| Clinical Grading (Radiance & Fine Lines) | X | In-Clinic Product Application | X | | X | In-Clinic Product Application | X |
| Corneometer Measurements | X | | X | X | X | | X |
| SKICON Measurements | X | | X | X | X | | X |
| Tewameter Measurements | X | | | | X | | |
| Cutometer Measurements | X | | X | X | X | | X |
| Self-Evaluation w/ VAS scale | X | | X | X | X | | X |
| Self-Assessment Questionnaires | X | | X | X | X | | X |
| In-Home Product Application | | | | X | | | |
| Daily Diaries | | | | X | | | |

BL = baseline,
PA = post-application

Subjects participated in the following procedures at each of the time points (unless otherwise indicated):

1) Clinical Grading of Efficacy Parameters: Subjects were clinically graded globally on the face for radiance, fine lines, and overall dryness.

2) Corneometer Measurements: Triplicate Corneometer CM 825 (Courage+Khazaka, Germany) measurements were taken on the center of each subject's cheek to measure the moisture content in the stratum corneum. Measurement is based on the capacitance measurement of a dielectric medium.

3) SKICON Measurements: Triplicate SKICON-200EX (I.B.S. Co., Ltd., Japan) measurements were taken on the center of each subject's cheek to measure test material effects on the moisture content of the stratum corneum. Measures conductance.

4) Tewameter Measurements: At pre-application on day 1 and day 8, a single Tewameter TM300 (Courage+Khazaka, Germany) measurement was taken on the center of each subject's cheek to assess passive water transport through the stratum corneum (transepidermal water loss [TEWL]). Measures the density gradient of water evaporation from the skin indirectly by 2 pairs of sensors (temperature and relative humidity).

5) Cutometer Measurements: A single Cutometer MPA 580 (Courage+Khazaka, Germany) measurement was taken on the lower edge of the orbit (directly beneath the center of the eye) of each subject to measure the viscoelastic properties of the skin. Measures elasticity.

6) Subject Rating of Skin Attributes: Subjects used a mirror to evaluate and rate specific facial skin attributes.

7) Self-Assessment Questionnaire: Subjects completed a Sponsor-provided self-assessment questionnaire regarding test material efficacy and attributes at each post-baseline time point.

Corneometer and Cutometer measurements were taken on 1 side of the face (right or left) and SKICON and Tewameter measurements were taken on the opposite side of the face, in accordance with a predetermined randomization.

Overall Conclusions: Overall results from this single-center, double-blind, clinical trial indicate that the Sponsor's test materials [Cell 1: Formulation 1505-21, Cell 2: Formulation 1505-42B, and Cell 3: Formulation benchmark/Amore Pacific] were effective in improving facial skin condition and moisturization over the course of 8 days of use by women with mild to moderate facial dry skin, fine lines, and skin dullness under the conditions of this test.

For clinical grading of efficacy parameters, all 3 cells showed a statistically significant increase (improvement) in scores for radiance and fine lines at each post-baseline time point (30 minutes post-application on day 1, 8 hours post-application on day 1, pre-application on day 8, and 30 minutes post-application on day 8) and for overall dryness at pre- and post-application on day 8 when compared with baseline (day 1 pre-application) scores.

All 3 cells produced a statistically significant improvement in the moisturization of the stratum corneum, with a statistically significant increase (improvement) in values for Corneometer and SKICON measurements at each post-baseline time point when compared with baseline values. For Tewameter measurements, there was a statistically significant decrease (improvement) for Cell 3 at day 8 pre-application and no statistically significant change from baseline for Cell 1 and Cell 2.

Analysis of the Cutometer measurements showed the following statistically significant differences when compared with baseline (day 1 pre-application) values: decrease in extensibility at 8 hours post-application on day 1 for Cell 3; increase in resiliency for Cell 2 at 8 hours post-application on day 1 and 30 minutes post-application on day 8; and increase in pure elasticity for Cell 1 and Cell 2 at 30 minutes post-application on day 8. Results of the Cutometer measurements indicate that Cell 1: Formulation 1505-21 and Cell 2: Formulation 1505-42B for helping improve skin elasticity and Cell 3: Formulation benchmark/Amore Pacific for helping improve skin firmness.

Analysis of the subject rating of skin attributes showed that subjects in all 3 cells indicated a statistically significant improvement in their perceptions of the following attributes at each post-baseline time point when compared with baseline response values: moisturization (feel and appearance), fine lines [excluding Cell 3 at 30 minutes post-application on day 1], radiance, suppleness, softness, smoothness, bouncy skin, dryness, overall appearance, and overall comfort. Analysis of the self-assessment questionnaires completed by subjects at post-baseline time points indicated that a statistically significant proportion of subjects in all 3 treatment cells selected favorable responses to almost all of the inquiries (regarding application experience, improvements in skin appearance and feel, comparison to past moisturizers used, etc.) at each asked time point.

Comparisons among the treatment cells indicated that all 3 test materials were generally equally effective for improving facial skin condition, providing moisturization, and subject perceptions (through rating of skin attributes and self-assessment questionnaires), although a few statistically significant differences were noted between treatment cells for efficacy parameter grading, Corneometer, and SKICON.

Procedures and Methods: During the course of the study, applicable clinic rooms were maintained at a temperature of 68° F. to 75° F. and the relative humidity ranged from 35% to 65%. After the acclimation period, candidate subjects were evaluated for the Fitzpatrick Skin Classification and the Presence of Facial Dryness/Aging.

The Fitzpatrick Skin Classification is based on the skin's unprotected response to the first 30 to 45 minutes of sun exposure after a winter season without sun exposure. Types I-VI qualified (approximately 80% of subjects having types I-IV and the remaining subjects having types V-VI). The categories of skin types are described in Table 15.

TABLE 15

Fitzpatrick Skin Classification

| Type | Physical Characteristics | Skin Reaction to UV |
| --- | --- | --- |
| I | White; very fair; red or blonde hair; blue eyes; freckles | Always burns easily; never tans |
| II | White; fair; red or blonde hair; blue, hazel, or green eyes | Always burns easily; tans minimally |
| III | Cream white; fair with any eye or hair color; very common | Burns moderately; tans gradually |
| IV | Brown; typical Mediterranean white skin | Burns minimally; always tans well |
| V | Dark Brown; mid-eastern skin types, black hair, olive skin | Rarely burns; tans profusely |
| VI | Black; black hair, black eyes, black skin | Never burns; deeply pigmented |

Presence of Facial Dryness/Aging: Clinically determined mild to moderate (score of 3-6 according to modified Griffiths' scale2 where 0=none and 9=severe) facial dryness, global facial fine lines, and facial skin dullness.

Evaluation Procedure:

1) Clinical Grading of Efficacy Parameters: Subjects were clinically graded for the following efficacy parameters globally on the face using a modified Griffiths' 10-point scale according to the following numerical definitions (with half-point scores assigned as necessary to accurately describe the skin condition): 0=none (best possible condition), 1 to 3=mild, 4 to 6=moderate, 7 to 9=severe (worst possible condition). The following parameters were graded according to the listed scale anchors: Radiance 0=Radiant, luminous appearance and 9=Dull/matte and or/sallow appearance, Fine lines 0=none and, 9=Numerous, deep fine lines, Overall dryness 0=Not dry, plump, smooth, soft feeling and 9=Severe dryness, dull, rough feeling, flaking/scaling.

2) Corneometer Measurements: Triplicate Corneometer CM 825 (Courage+Khazaka, Germany) measurements were taken on the center of each subject's cheek (at the intersection of lines extending down from the outer corner of the eye and horizontally across the bottom of the nose) to measure product hydration effects on the skin surface. The Corneometer measures moisture content in the stratum corneum by an electrical capacitance method. The measurement has no units, but is proportional to the dielectric constant of the surface layers of the skin, and increases as the skin becomes more hydrated. The readings are directly related to the skin's electrical capacitance (picofarads).

3) SKICON Measurements: Triplicate SKICON-200EX (I.B.S. Co., Ltd., Japan) measurements were taken on the center of each subject's cheek (at the intersection of lines extending down from the outer corner of the eye and horizontally across the bottom of the nose) to measure test material effects on the moisture content of the stratum corneum. SKICON measures test material effects on the moisture content in the stratum corneum using high frequency conductance methodology. Data is collected in micro Siemens (0), and measurements increase with skin hydration.

4) Tewameter Measurements: A single Tewameter TM300 (Courage+Khazaka, Germany) measurement was taken on the center of each subject's cheek (at the intersection of lines extending down from the outer corner of the eye and horizontally across the bottom of the nose) to assess passive water transport through the stratum corneum (transepidermal water loss [TEWL]). The measurement of this water evaporation is based on the diffusion principle in an open chamber, and the density gradient is measured indirectly by 2 pairs of sensors located inside the hollow cylinder probe. Data are analyzed by a microprocessor and reported in g/m2/h. A decrease in TEWL values reflects an improvement in the barrier properties of the skin.

5) Cutometer Measurements: A single Cutometer MPA 580 (Courage+Khazaka, Germany) measurement was taken on the lower edge of the orbit (directly beneath the center of the eye) of each subject to measure the viscoelastic properties of the skin. Negative pressure of 300 mbar was applied and released through an 8-mm probe (standard settings). The measurement lasts for 30 seconds, during which are 2 repeated cycles of a 5-second on (vacuum) time and a 10-second off (skin release) time. The movement of the skin into and out of the probe was recorded during the application and release of suction. The amount of extensibility, resiliency, pure elasticity and biological elasticity were recorded.

6) Subject Rating of Skin Attributes: Subjects used a mirror to evaluate and rate specific facial skin attributes according to a 10-point scale where 1=worst condition and 10=best condition.

Subjects were instructed to follow their normal morning skin care routine and to apply the assigned test material to the entire face every evening after cleansing and toning. Subjects were distributed a pre-weighed unit of the cell-specific test material and written/verbal usage instructions: Cell 1 (Formulation 1505-21)—Before each use, twist open the base of the cap of the Essence counterclockwise. Once twisted off, push down on the button on top of the cap to expel the entire contents of the dropper into the palm of your hand. Rub hands together and with both hands smooth product evenly over your entire face and allow to dry. Use 1 pump per application. Follow with the rest of your nighttime skincare regimen. Do not apply essence on eye lids. Avoid getting into eyes. Cell 2 (Formulation 1505-42B)—Apply 1-2 pumps of product evenly to your entire face. Follow with the rest of your nighttime skincare regimen. Cell 3 (Formulation benchmark/Amore Pacific)—Apply 1-2 pumps of product evenly to your entire face. Follow with the rest of your nighttime skincare regimen.

Subjects performed the first application of the assigned test material in the clinic, under the supervision of clinic personnel. Approximately 30 minutes after application, clinical grading of efficacy parameters, bioinstrumentation measurements (Corneometer, SKICON, and Cutometer), and subject rating of skin attribute procedures were repeated as described for baseline. Additionally, subjects completed a Sponsor-provided self-assessment questionnaire regarding test material efficacy and attributes.

Subjects were provided with a calendar of study visits and a daily diary to record product application times and comments. Subjects were instructed not to apply any products to the face or engage in any activity which may remove the test material from the face (cleansing, exercise/sweat, etc.) until after completion of visit 2 (day 1/hour 8).

Subjects returned to the clinic for visit 2 (day 1), approximately 8 hours after test material application. Clinic personnel recorded concomitant medications, questioned subjects regarding changes in their health, and AEs were recorded if applicable.

Subjects acclimated to ambient temperature and humidity conditions for at least 15 minutes and then participated in the following evaluations as described for baseline: clinical grading of efficacy parameters, bioinstrumentation measurements (Corneometer, SKICON, and Cutometer), and subject rating of skin attributes. Subjects also completed a Sponsor-provided self-assessment questionnaire.

Subjects returned to the clinic for visit 3 (day 8) and participated in the following procedures: Clinic personnel recorded concomitant medications and questioned subjects regarding changes in their health. AEs were recorded if applicable. Daily diaries were collected, reviewed for compliance, and retained by the clinic. Subjects acclimated for at least 15 minutes and then participated in the following evaluation procedures as described for baseline: Clinical grading of efficacy parameters was performed. Bioinstrumentation measurements (Corneometer, SKICON, Tewameter, and Cutometer) were performed. Subjects rated skin attributes and completed a Sponsor-provided self-assessment questionnaire. After completion of day 8 baseline (pre-application) procedures, subjects performed an in-clinic application of the test material. Test material units were collected, visually inspected and weighed for compliance, and retained by the clinic. Approximately 30 minutes after test material application, clinical grading of efficacy parameters, bioinstrumentation measurements (Corneometer, SKICON, and Cutometer), subject rating of skin attributes, and subject completion of Sponsor-provided self-assessment questionnaire were repeated.

Results

Figure 9A:
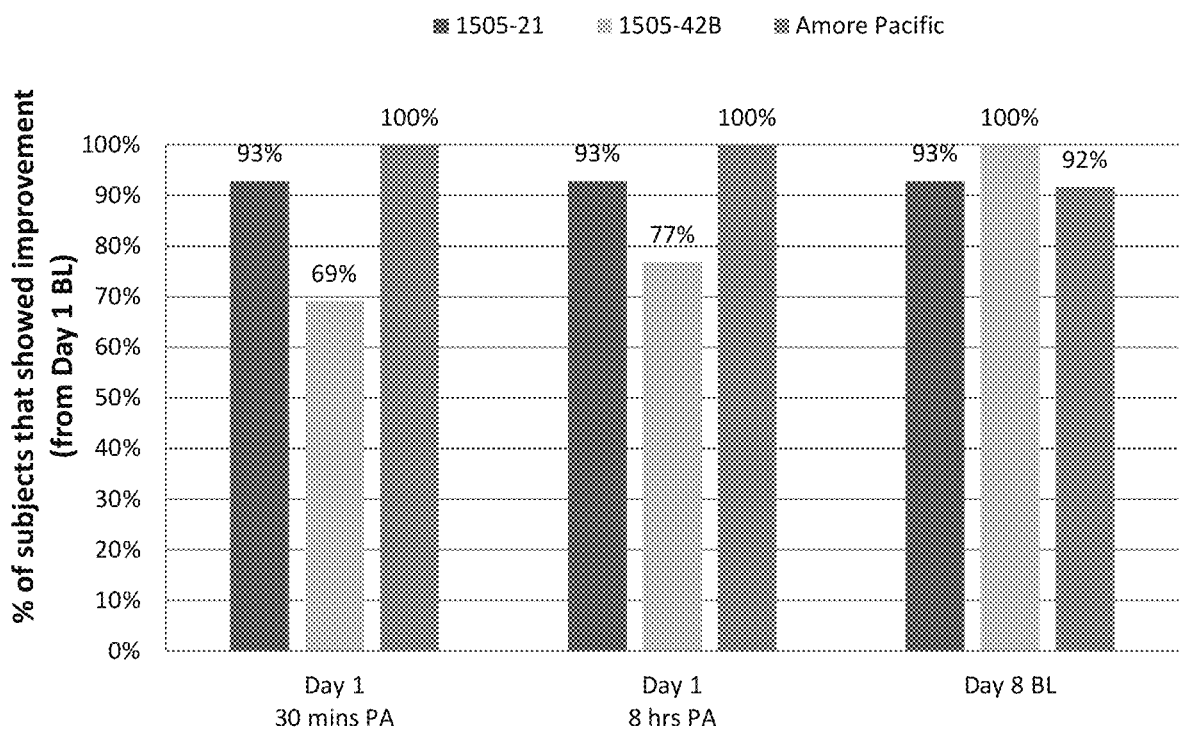
FIG. 9A) Demonstrates improvement in radiance after 1 week.
Figure 9B:
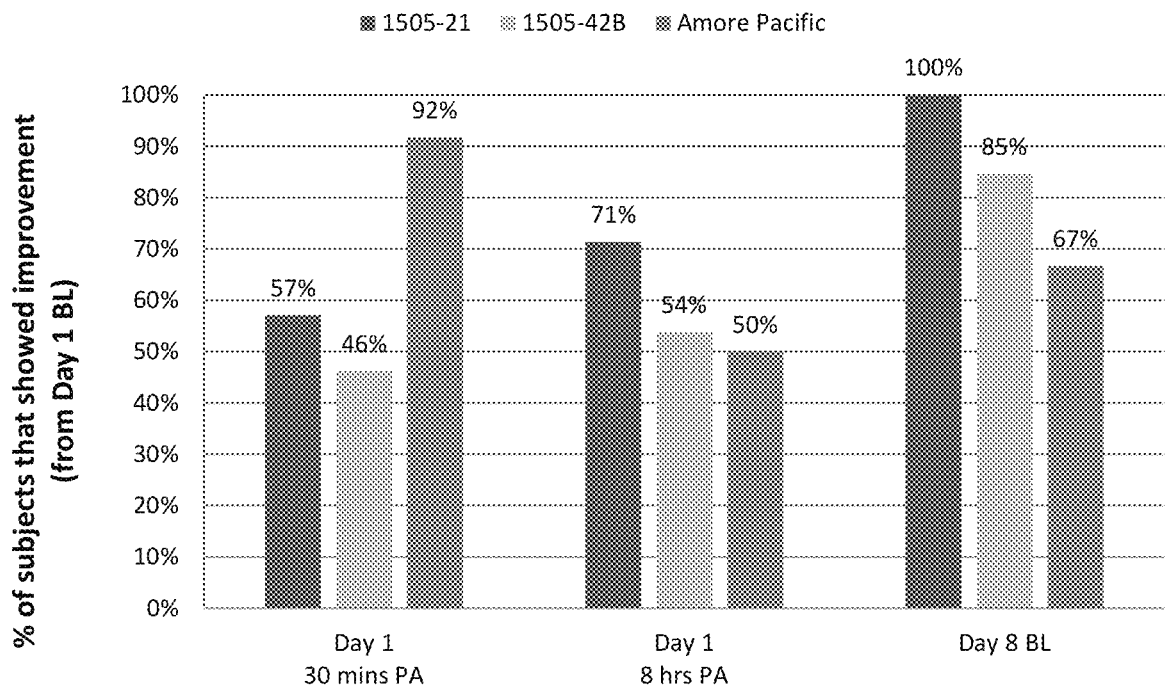
FIG. 9B) Demonstrates improvement in fine lines after 1 week.

Efficacy Parameter Clinical Grading: Use of the Sponsor's test materials [Cell 1: Formulation 1505-21, Cell 2: Formulation 1505-42B, and Cell 3: Formulation benchmark/Amore Pacific] produced a statistically significant decrease (improvement) in clinical grading scores for radiance and fine lines at each post-baseline time point (30 minutes post-application on day 1, 8 hours post-application on day 1, pre-application on day 8, and 30 minutes post-application on day 8) when compared with baseline (day 1 pre-application) scores, see FIG. 9A (radiance) and 9B (fine lines). For grading of overall dryness, there was a statistically significant decrease (improvement) in scores for Cell 3: Formulation benchmark/Amore Pacific at all post-baseline time points and for Cell 1: Formulation 1505-21 and Cell 2: Formulation 1505-42B at pre-application and 30 minutes post-application on day 8 when compared with baseline scores. [Note that due to the timing of the protocol amendment implementation, only 1 subject in cells 1 and 2 were graded at the 30 minute and 8 hour post-application time points on day 1, which is why there are no statistically significant changes from baseline for these cells and time points.] Comparisons among the treatment cells, based on the mean change from baseline for efficacy parameters, indicated that Cell 3 produced a statistically significant greater improvement in radiance and fine lines at 30 minutes post-application on day 1 compared to Cell 1 and Cell 2, and in overall dryness at 30 minutes post-application on day 8 compared to Cell 1.

Figure 10:
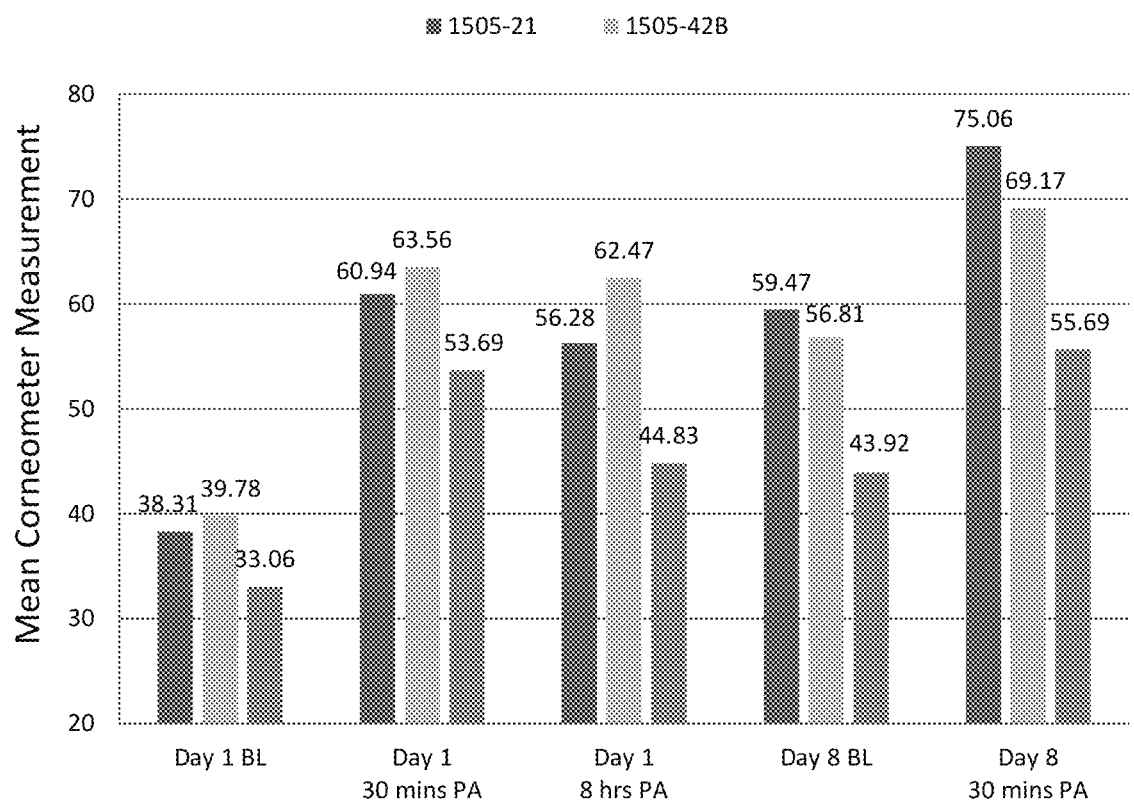
FIG. 10 depicts the improvement in moisture as measured by capacitance using the Corneometer over the course of the study.
Figure 11A:
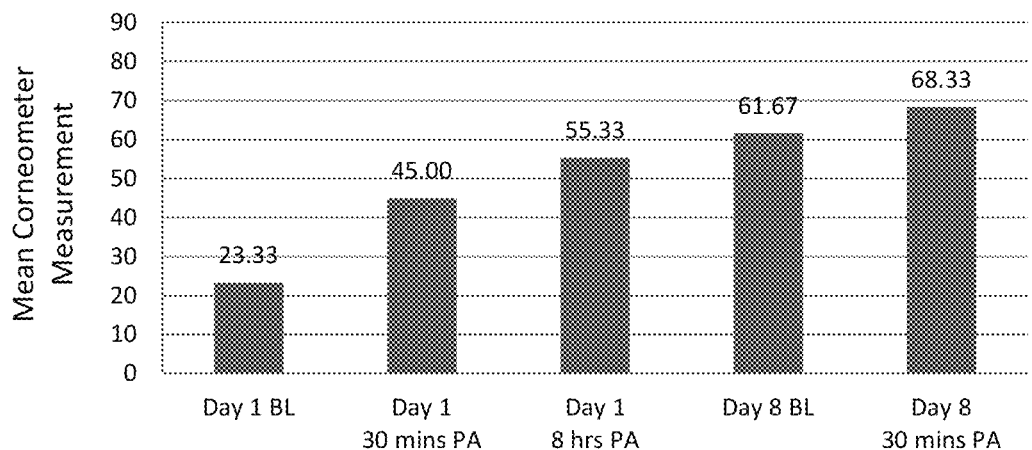
FIG. 11A) Subject #7 with baseline severe dry skin.
Figure 11B:
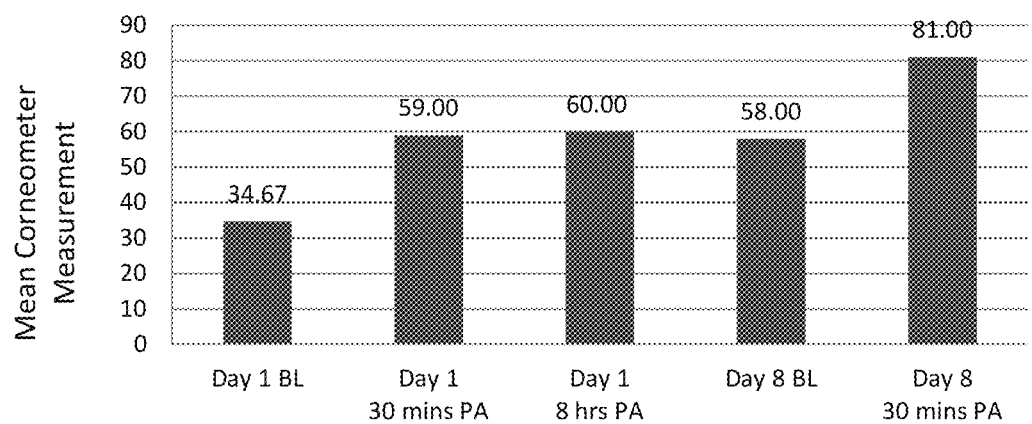
FIG. 11B) Subject #16 with baseline moderate dry skin.
Figure 11C:
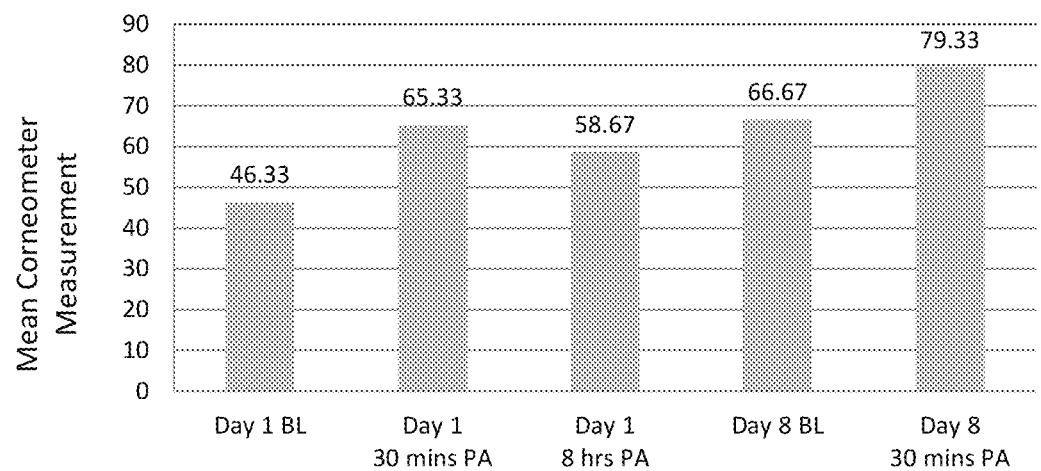
FIG. 11C) Subject #14 with baseline mild dry skin.

Corneometer Measurements: Use of the Sponsor's test materials [Cell 1: Formulation 1505-21, Cell 2: Formulation 1505-42B, and Cell 3: Formulation benchmark/Amore Pacific] produced a statistically significant increase (improvement) in Corneometer measurement values at each post-baseline time point (30 minutes post-application on day 1, 8 hours post-application on day 1, pre-application on day 8, and 30 minutes post-application on day 8) when compared with baseline (day 1 pre-application) values. Comparisons among the treatment cells, based on the mean change from baseline for Corneometer measurements, indicated no statistically significant differences among the treatment cells at any time points. See FIG. 10. FIGS. 11A, 11B, and 11C represent 3 subjects, each demonstrating that the moisture level of the individuals skin adjusted to an individualized level.

Figure 12:
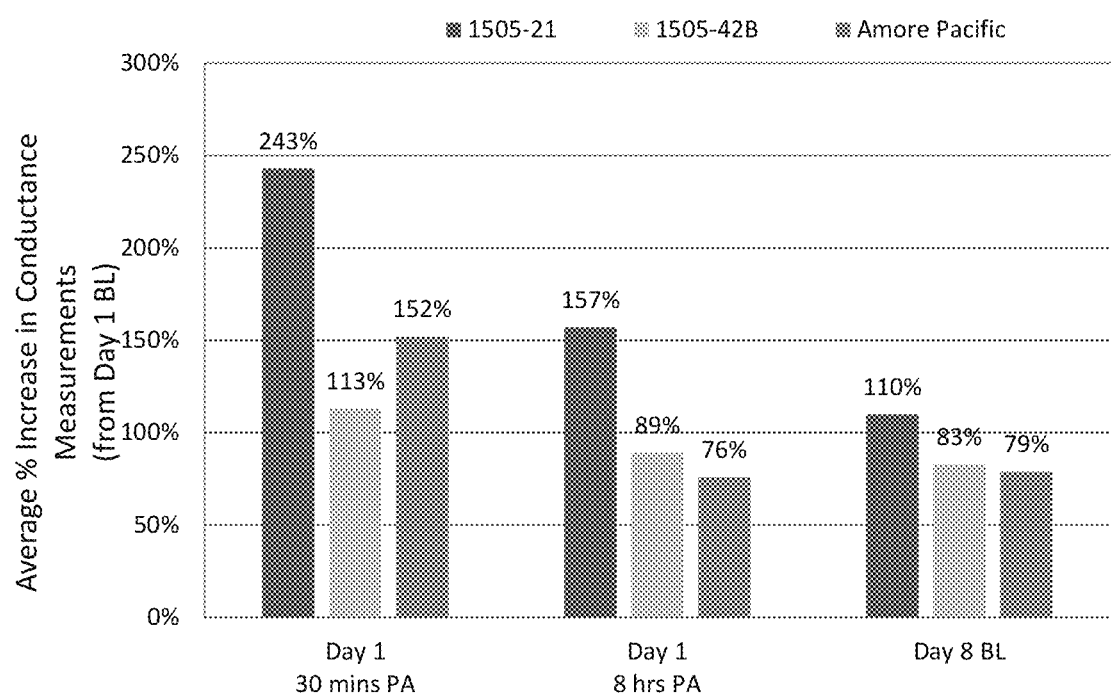
FIG. 12 depicts improvement in conductance moisture measurements using the SKICON test.

SKICON Measurements: Use of the Sponsor's test materials [Cell 1: Formulation 1505-21, Cell 2: Formulation 1505-42B, and Cell 3: Formulation benchmark/Amore Pacific] produced a statistically significant increase (improvement) in SKICON measurement values at each post-baseline time point (30 minutes post-application on day 1, 8 hours post-application on day 1, pre-application on day 8, and 30 minutes post-application on day 8) when compared with baseline (day 1 pre-application) values, see FIG. 12. Comparisons among the treatment cells, based on the mean change from baseline for SKICON measurements, indicated that Cell 1 produced a statistically significant greater improvement at 30 minutes and 8 hours post-application on day 1 compared to Cell 2 and Cell 3, and at 30 minutes post-application on day 8 compared to Cell 3.

Tewameter Measurements: Use of the Sponsor's test material for Cell 3: Formulation benchmark/Amore Pacific produced a statistically significant decrease (improvement) in Tewameter measurement values at day 8 pre-application when compared with baseline (day 1 pre-application) values. There were no statistically significant changes from baseline in TEWL values for Cell 1: Formulation 1505-21 and Cell 2: Formulation 1505-42B at day 8 pre-application. Comparisons among the treatment cells, based on the mean change from baseline for Tewameter measurements, indicated no statistically significant differences among the treatment cells at day 8 pre-application.

Figure 13:
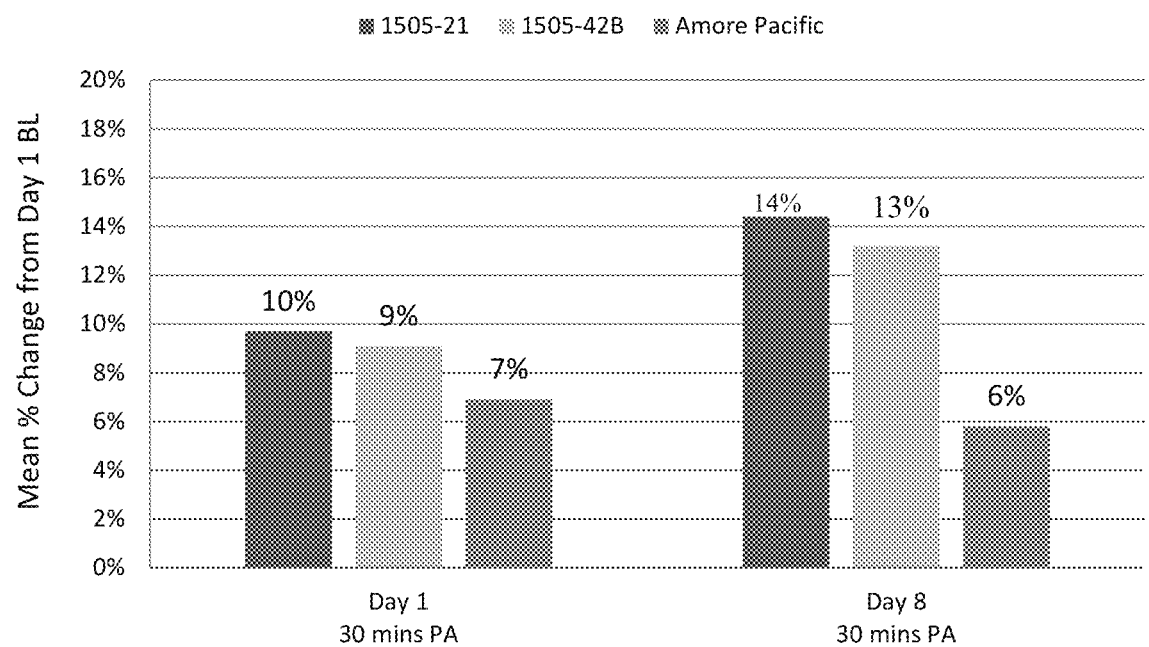
FIG. 13 depicts the improvements in skin elasticity after 1 week measured by the Cutometer.

Cutometer Measurements: Analysis of the Cutometer measurements for each treatment cell showed the following statistically significant differences (improvements) when compared with baseline (day 1 pre-application) values: Extensibility (R0): decrease for Cell 3 at 8 hours post-application on day 1, Resiliency (R2): increase for Cell 2 at 8 hours post-application on day 1 and 30 minutes post-application on day 8, Pure Elasticity (R5), see FIG. 13: increase for Cell 1 and Cell 2 at 30 minutes post-application on day 8. There were no statistically significant changes from baseline for biological elasticity (R7) at any post-baseline time point for any of the treatment cells. Comparisons among the treatment cells, based on the mean change from baseline for Cutometer measurements, indicated no statistically significant differences among the treatment cells at any post-baseline time point.

Figure 14A:
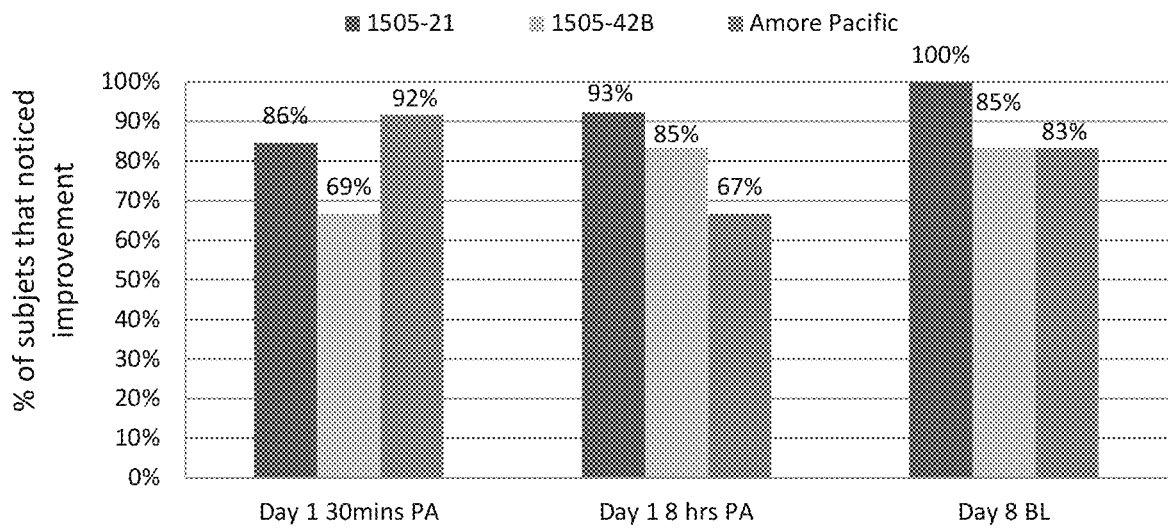
FIG. 14A) Improvement in radiance after 1 week.
Figure 14B:
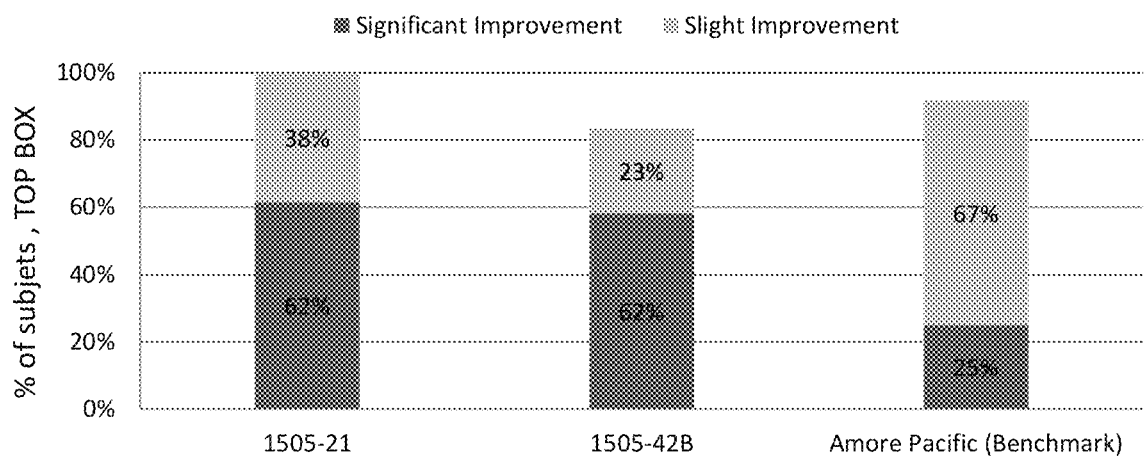
FIG. 14B) Reported improvement in firmness.
Figure 14C:
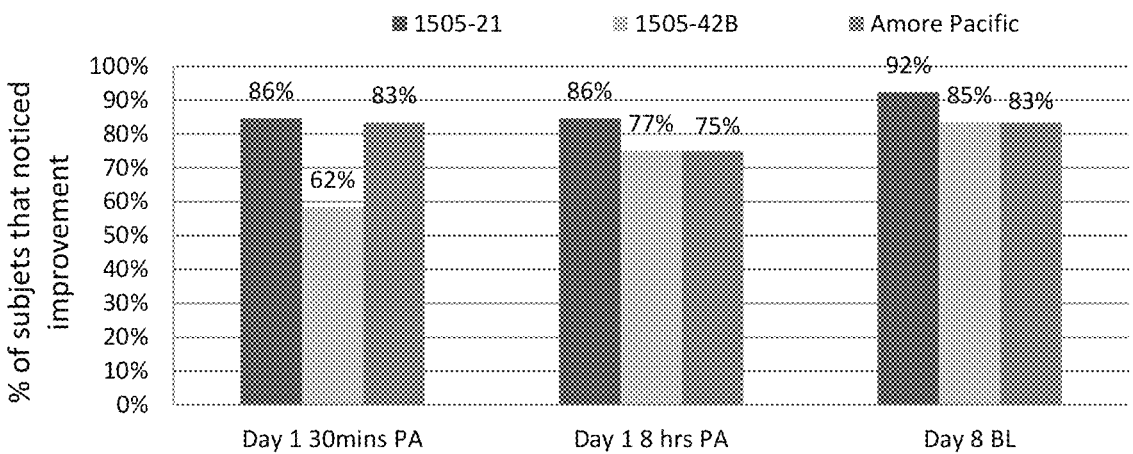
FIG. 14C) Improvement in plumpness after 1 week.

Subject Rating of Skin Attributes: Use of the Sponsor's test materials [Cell 1: Formulation 1505-21, Cell 2: Formulation 1505-42B, and Cell 3: R Formulation benchmark/Amore Pacific] produced a statistically significant increase (improvement) in subject response values for the following attributes at each post-baseline time point (30 minutes post-application on day 1, 8 hours post-application on day 1, pre-application on day 8, and 30 minutes post-application on day 8) when compared with baseline (day 1 pre-application) values (unless otherwise indicated): Moisturization (skin feel), Moisturization (appearance), Fine lines (appearance)—excluding Cell 3 at 30 minutes post-application on day 1, Radiance (appearance, see FIG. 14A), Suppleness (elasticity, snap back, firmness, see FIG. 14B), Softness (to touch), Smoothness (to touch), Bouncy skin (to touch, see FIG. 14C), Dryness (appearance), Overall appearance, Overall comfort (feel). There was also a statistically significant improvement in response values for "Tightness" for Cell 2 at all time points and for Cell 3 at 8 hours post-application on day 1 and 30 minutes post-application on day 8 when compared with baseline values. Comparisons among the treatment cells, based on the mean change from baseline for skin attribute rating parameters, indicated no statistically significant differences among the treatment cells at any post-baseline time point.

Self-Assessment Questionnaire: Results of the analyses of the self-assessment questionnaires completed by subjects at each post-baseline time point showed that a statistically significant proportion of subjects in all 3 cells selected favorable responses compared to unfavorable responses at the indicated time points (unless otherwise indicated). Comparisons among the treatment cells, based on the proportion of favorable responses, showed that a greater proportion of subjects in Cell 3 selected favorable responses compared to Cell 2 for the question "Did you notice a difference in how youthful your skin looks after using the product?" at 30 minutes post-application on day 1.

Discussion and Conclusions

Figure 15:
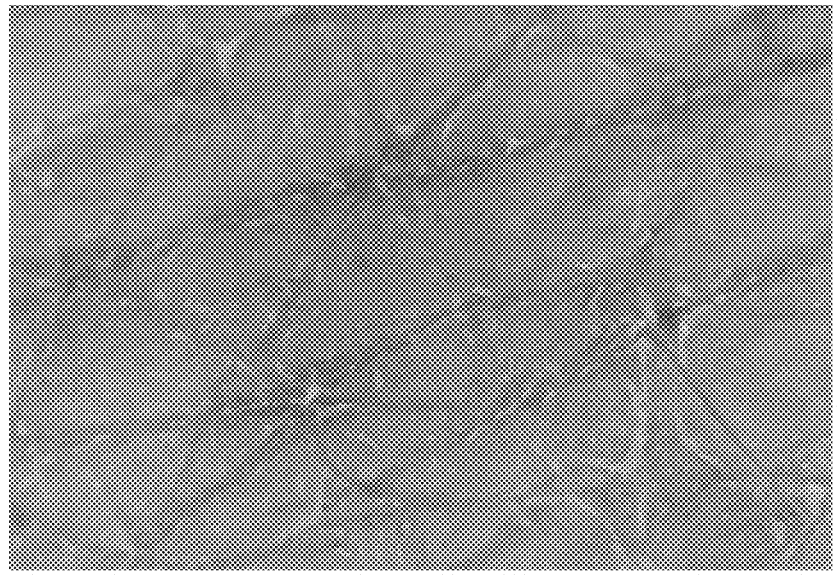
FIG. 15 provides a photograph of severe dry skin prior to the application of a moisturizing composition and a photograph of skin 15 minutes after the application of formulation 1505-21.
Figure 15:
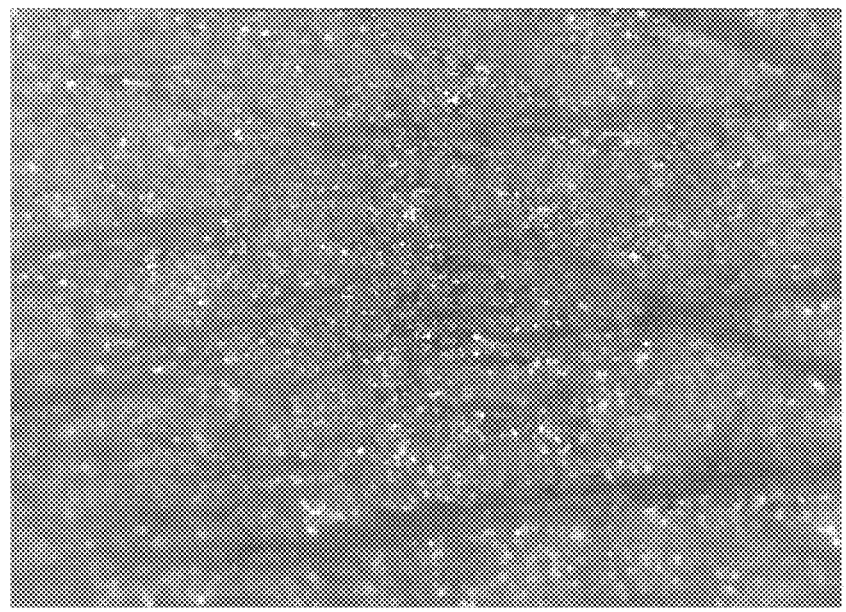

Overall results from this single-center, double-blind, clinical trial indicate that the Sponsor's test materials [Cell 1: Formulation 1505-21, Cell 2: Formulation 1505-42B, and Cell 3: Formulation benchmark/Amore Pacific] were effective in improving facial skin condition and moisturization over the course of 8 days of use by women with mild to moderate facial dry skin, fine lines, and skin dullness under the conditions of this test. FIG. 15 shows the photograph of dry skin before and 15 minutes after the application of Formulation 1505-21.

For clinical grading of efficacy parameters, all 3 cells showed a statistically significant increase (improvement) in scores for radiance and fine lines at each post-baseline time point (30 minutes post-application on day 1, 8 hours post-application on day 1, pre-application on day 8, and 30 minutes post-application on day 8) and for overall dryness at pre- and post-application on day 8 when compared with baseline (day 1 pre-application) scores.

All 3 cells produced a statistically significant improvement in the moisturization of the stratum corneum, with a statistically significant increase (improvement) in values for Corneometer and SKICON measurements at each post-baseline time point when compared with baseline values. For Tewameter measurements, there was a statistically significant decrease (improvement) for Cell 3 at day 8 pre-application and no statistically significant change from baseline for Cell 1 and Cell 2.

Analysis of the Cutometer measurements showed the following statistically significant differences when compared with baseline (day 1 pre-application) values: decrease in extensibility at 8 hours post-application on day 1 for Cell 3; increase in resiliency for Cell 2 at 8 hours post-application on day 1 and 30 minutes post-application on day 8; and increase in pure elasticity for Cell 1 and Cell 2 at 30 minutes post-application on day 8. Results of the Cutometer measurements indicate that Cell 1: Formulation 1505-21 and Cell 2: Formulation 1505-42B for helping improve skin elasticity and Cell 3: Formulation benchmark/Amore Pacific for helping improve skin firmness.

Analysis of the subject rating of skin attributes showed that subjects in all 3 cells indicated a statistically significant improvement in their perceptions of the following attributes at each post-baseline time point when compared with baseline response values: moisturization (feel and appearance), fine lines (excluding Cell 3 at 30 minutes post-application on day 1), radiance, suppleness, softness, smoothness, bouncy skin, dryness, overall appearance, and overall comfort. Analysis of the self-assessment questionnaires completed by subjects at post-baseline time points indicated that a statistically significant proportion of subjects in all 3 treatment cells selected favorable responses to almost all of the inquiries (regarding application experience, improvements in skin appearance and feel, comparison to past moisturizers used, etc.) at each asked time point.

Comparisons among the treatment cells indicated that all 3 test materials were generally equally effective for improving facial skin condition, providing moisturization, and subject perceptions (through rating of skin attributes and self-assessment questionnaires), although a few statistically significant differences were noted between treatment cells for efficacy parameter grading, Corneometer, and SKICON.

Example 12: Treating Xerosis with a Novel Interpenetrating Polymer Network

Xerosis, or abnormally dry skin, can stem from a variety of causes from the environment to underlying medical conditions and humectants are commonly used to treat this dry, itchy and flaky skin. Glycerol and hyaluronic acid (HA) are widely used as humectants but often simply deposit at the surface of the skin being too hydrophilic to interact with the dry, hydrophobic and compacted stratum corneum. This work set out to improve the delivery of glycerol and HA by designing a hydrophobically-modified interpenetrating polymer network (IPN) for superior substantivity, delivery and hydration at the stratum corneum.

Figure 16A:
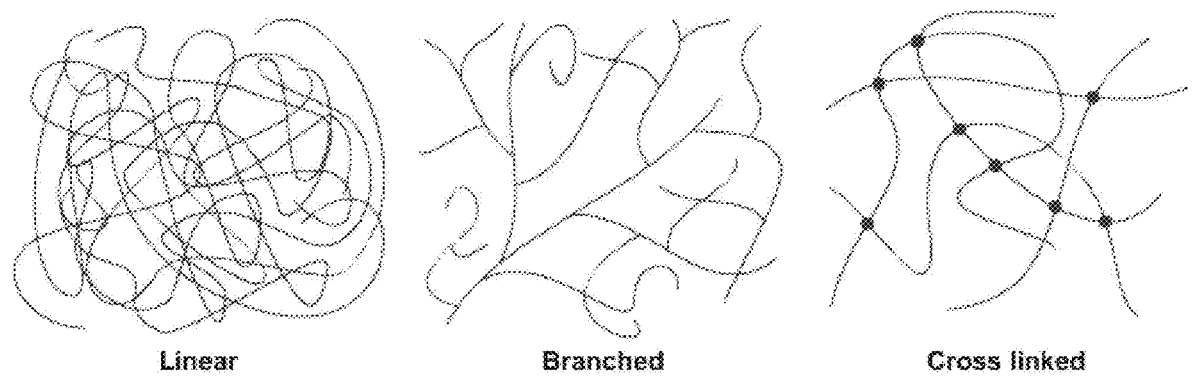
FIG. 16A depicts the linear, branched, and crosslinked polymers, polypeptides, and polysaccharides in embodiments described herein.
Figure 16B:
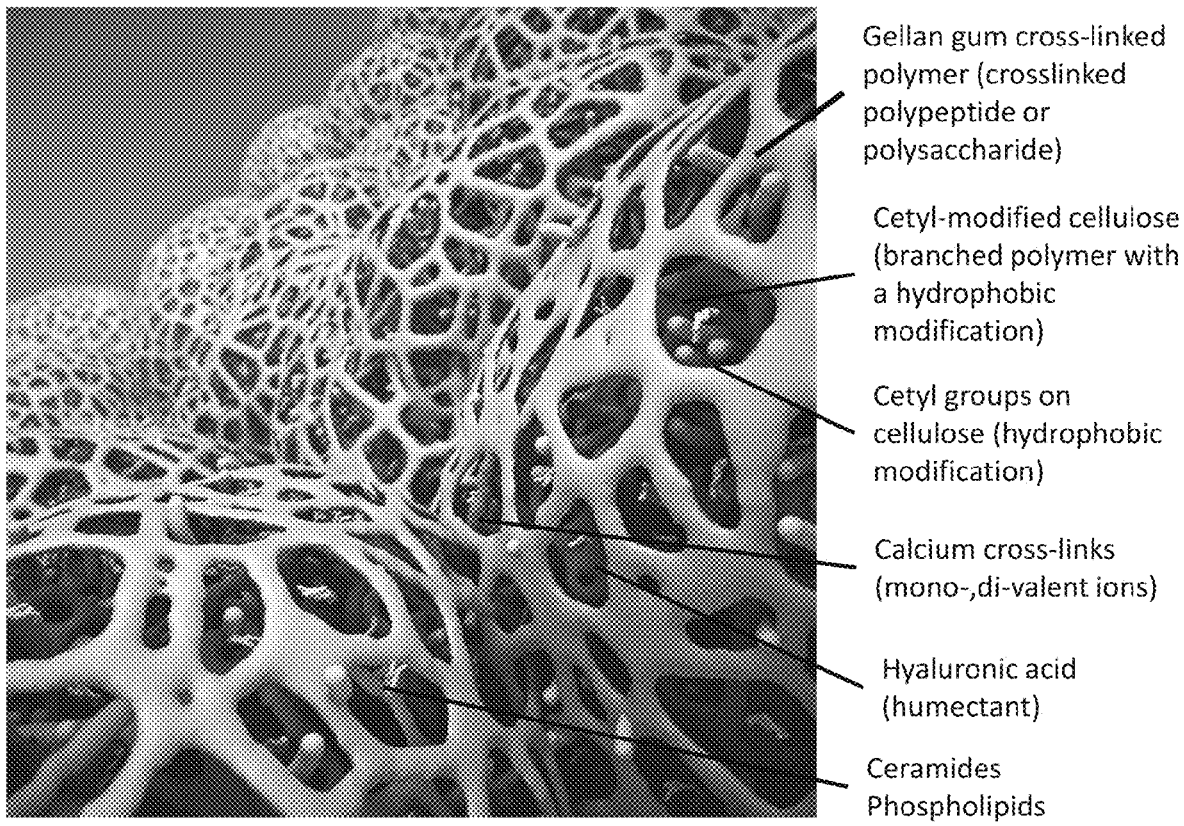
FIG. 16B is a chemistry depiction of the 3D3P interpenetrating polymer network.

A 3D3P (3 dimensional 3 polymer)-IPN (interpenetrating polymer network), chemically depicted in FIG. 16B, was created from gellan gum, hydrophobically-modified cellulose and a linear sodium hyaluronate. Magnesium and calcium ions were added in the form of PCA salts to cross-link the gellan gum forming a gelatinous 3D3P-IPN. Glycerol was introduced to attract and bind water and calcium ions, as a salt of pyroglutamic acid, to support barrier homeostasis. The super-humectant 3D3P-IPN composition was examined with both in vitro and in vivo techniques to determine the effectiveness in restoring hydration levels at the stratum corneum and the capacity to attract and bind water molecules.

Methods:

Karl Fischer and Dynamic Vapor Sorption (DVS) Analysis: Dynamic vapor sorption (DVS) technique was utilized to study water sorption characteristics of 3D3P-IPN versus glycerol and a mixture of glycerol and sodium hyaluronate, which are commercially common humectants formulated in moisturizing products. It should be noted that it was found that the 3D3P-IPN composition could not be fully dehydrated in a drying oven (105° C.) prior to starting the sorption study. Percent moisture concentration was analyzed in each sample with a Karl Fisher titration technique. The samples where then exposed to an increasing relative humidity (RH) over a period of 1200 minutes while measured for weight gain/loss with respect to RH and time. The Karl Fischer analysis was performed using a Mettler Toledo model V20 volumetric titrator interfaced with a D0308 drying oven for the drying stage of analysis. The oven set at 260° C. A nitrogen stream set a flow rate of 50 mL/minute was used to transfer the moisture from the sample to the titration vessel.

In vivo Capacitance: A leading commercial moisturizer product control was selected with a high concentration of glycerol and a mixture of other humectants including sodium hyaluronate, hydroxyethyl cellulose, butylene glycol, betaine, beta-glucan, magnesium aspartate, zinc gluconate, copper gluconate, and calcium gluconate to compare against the 3D3P-IPN delivery scaffold for skin hydration. A corneometer capacitance technique was used to measure the changes in hydration over an eight day period on twelve human subjects ranging in mild to severe dry skin conditions.

Results:

The ability of 98% glycerol in 1.3% 3D3P-IPN to absorb moisture was determined by dynamic vapor sorption (DVS) and compared to 98% glycerol alone and 98% glycerol plus 1.3% sodium hyaluronate. Percent moisture concentration was analyzed in each sample with a Karl Fisher titration technique. The samples where then exposed to an increasing relative humidity (RH) over a period of 1200 minutes while measured for weight gain/loss with respect to RH and time. The 1.3% 3D3P-IPN plus 30% glycerol in water absorbed significantly more moisture (31.75%) than 98% glycerol (1.40-1.49%) and 98% glycerol plus 1.3% sodium hyaluronate (1.80-1.89%). This DVS data demonstrates that the 3D3P-IPN is capable of increasing the hygroscopic properties of glycerol.

Figure 17:
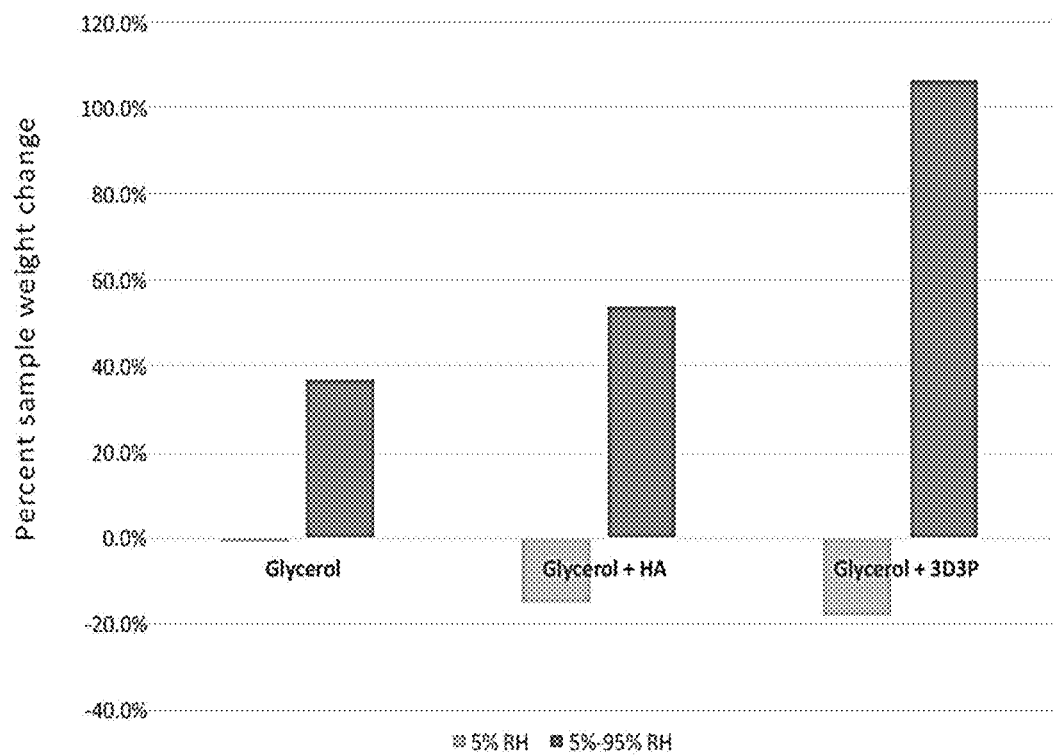
FIG. 17 shows the percent sample weight change by sorption under 5% relative humidity (RH) and 5%-95% RH.

When all three samples were equilibrated to 5% RH each lost further moisture increasing in loss from glycerol alone to glycerol plus sodium hyaluronate to glycerol plus 3D3P-IPN (FIG. 17). It was subsequently observed that the 3D3P-IPN composition in glycerol with other humectants was capable of absorbing a significantly greater amount of water during the period when the sample was exposed to a starting relative humidity of 5% which increased over time to 95% (FIG. 17).

A corneometer capacitance technique was used to measure the changes in hydration over an eight-day period on twelve subjects with mild to severe dry skin with daily use of 30% glycerol 3D3P-IPN. Hydration increased from a baseline average (38.31) after one application (60.94) which was maintained throughout the day (56.29). On day 8 before application, this level was still maintained (59.47) and 30 minutes after application, this rose to a peak level (75.06).

Figure 18:
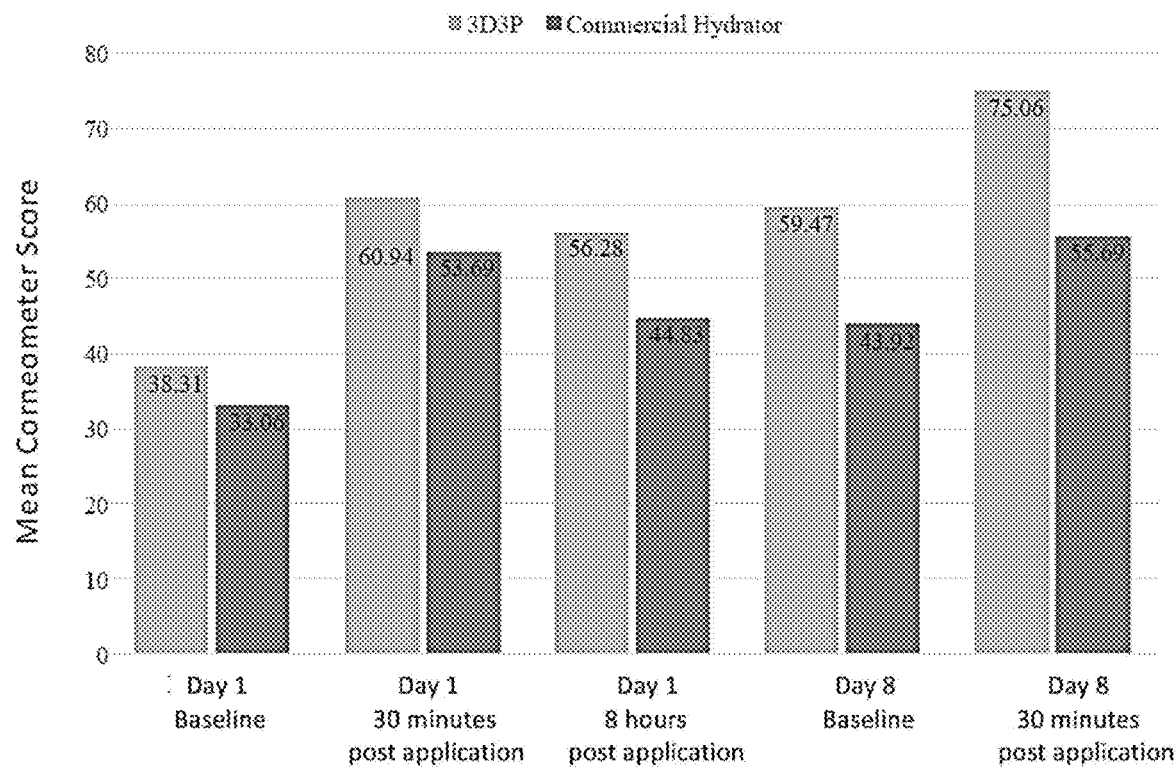
FIG. 18 shows the mean corneometry scores for once daily use of 3D3P-IPN and commercial hydration product.

FIG. 18 shows that both the commercial hydration product and 3D3P-IPN 30% glycerol produced and increase in skin surface hydration 30 minutes post first application. Of interest is that this moisture is better retained in the 3D3P-IPN glycerol subjects at the end of day one, produces a more elevated moisture level through continued use and results in an increased cumulative moisture level after 8 days at baseline. It should also be noted the subsequent rise post application producing a different in relative scores of 55.69 for the commercial product versus 75.06 for 3D3P-IPN glycerol.

Conclusion:

An interpenetrating polymer network can be created with gellan gum, modified cellulose and sodium hyaluronate stabilized with calcium and magnesium (3D3P-IPN). Glycerol and hyaluronic acid can be enhanced in both hydroscopic properties and skin hydrating performance when entrapped in a highly substantive IPN. When combined with 30% glycerol 3D3P-IPN can attract and retain moisture more effectively than 98% glycerol an 98% glycerol plus hyaluronic acid. 3D3P-IPN 30% glycerol can improve the moisture level of the skin surface more effectively in the short term and with continued use than a leading hydrating commercial product. The ability for an IPN to attract moisture to the skin and retain it at the skin's surface provides an improved system to support a key dermatological endpoint of generating and maintaining a well hydrated stratum corneum. This benefit is demonstrated in FIG. 15.

Example 13: Treating Roughness with a Novel Interpenetrating Polymer Network

VisioScan Imaging Procedures: VisioScan VC 98 (Courage+Khazaka electronic GmbH), which is a UVA-light (340-400 nm) video camera with high resolution was utilized to study the skin surface directly, and to capture images of each subject's right cheek. The image captures skin surface texture, dryness, and pigmentation. The imaging area is 6 mm×8 mm at a resolution of 480×640 pixels. VisioScan software was used to calculate and analyze the images for skin texture/roughness parameters.

Figure 19:
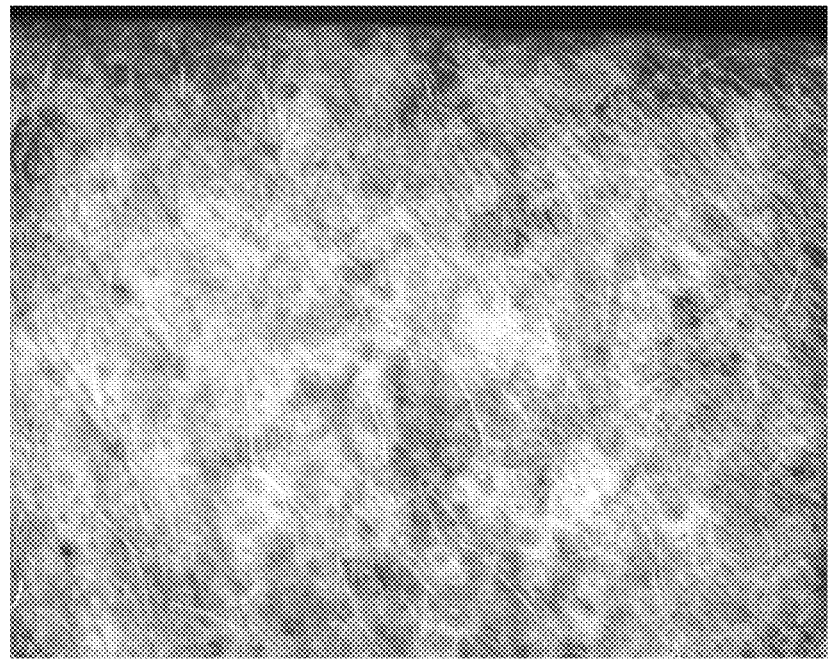
FIG. 19 shows VisioScan images for baseline and 8 weeks after treatment with formulation 1505-42B.
Figure 19:
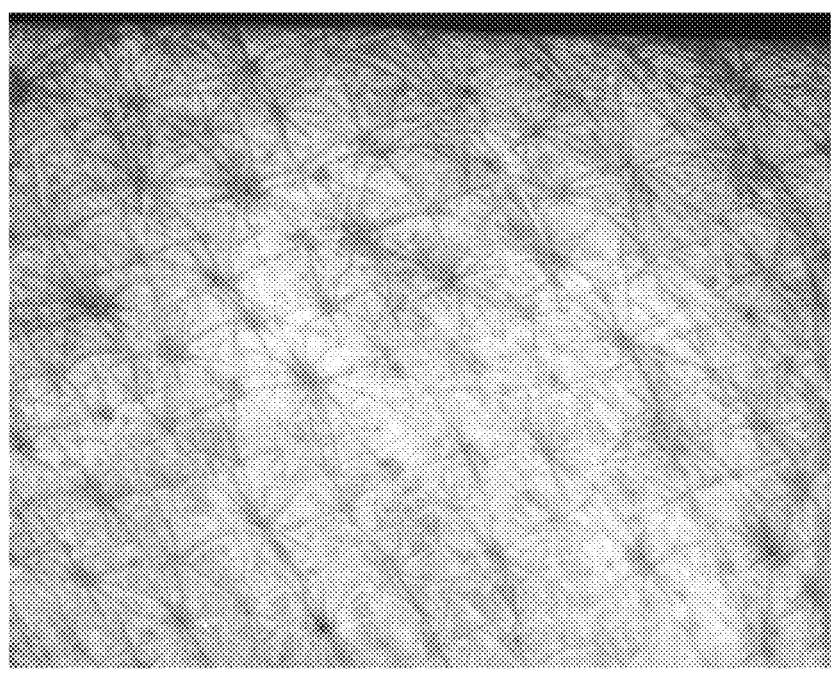

Analysis of the VisioScan images for roughness parameters (measurements R1-R5) showed no statistically significant differences from baseline (using paired t-test) for Cell 1 (Hydration+REDEFINE, formulation 1505-21). However, a statistically significant decrease (indicating an improvement in skin roughness) was observed in maximum roughness at weeks 4 and 8, in average roughness at week 8, in smoothness depth at week 4, and in arithmetic average roughness at week 4 for Cell 2 (Hydration+REVERSE, formulation 1505-42B) from baseline. See FIG. 19, top VisioScan image is baseline and the bottom VisioScan image is 8 weeks after treatment with formulation 1505-42B.

What is claimed:

1. An interpenetrating polymer network moisturizing topical composition comprising:
   about 0.01% w/w to about 5% w/w of crosslinked gellan gum;
   about 0.01% w/w to about 5% w/w of cetyl hydroxyethylcellulose;
   about 0.01% w/w to about 5% w/w of sodium hyaluronate;
   about 0.01% w/w to about 5% w/w of a mono-, or di-valent ion; and
   about 25% w/w to about 80% w/w of a humectant selected from glycerin, diglycerin, and a combination thereof;

wherein the cetyl hydroxyethylcellulose and the sodium hyaluronate are interlaced; and wherein the crosslinked gellan gum is crosslinked via ionic bonds, through the mono-, or di-valent ion, and entraps the interlaced cetyl hydroxyethylcellulose, the sodium hyaluronate, and the humectant to form the interpenetrating polymer network moisturizing topical composition.

2. The moisturizing topical composition of claim 1, wherein the mono-, or di-valent ion is selected from the group consisting of 2-Pyrrolidone-5-Carboxylic Acid (PCA), calcium PCA, sodium PCA, zinc PCA, magnesium PCA, sea salt, inorganic salts of citric acid, inorganic salts of lactic acid, calcium ascorbate, magnesium ascorbate, calcium oxide, calcium benzoate, calcium sorbate, calcium aspartate, magnesium carbonate, magnesium chloride, magnesium nitrate, and any combination thereof.

3. The moisturizing topical composition of claim 1, wherein the moisturizing composition is selected from the group consisting of liquid, solution, emulsion, suspension, triturate, jelly, foam, paste, ointment, shampoo, adhesive, cream, serum, milk, lotion, salve, oil, butter, gel, and balm.

4. A method of treating dry and/or irritated skin comprising administering an interpenetrating polymer network moisturizing topical composition comprising:
about 0.01% w/w to about 5% w/w of crosslinked gellan gum;
about 0.01% w/w to about 5% w/w of cetyl hydroxyethylcellulose;
about 0.01% w/w to about 5% w/w of sodium hyaluronate;
about 0.01% w/w to about 5% w/w of a mono-, or di-valent ion; and
about 25% w/w to about 80% w/w of a humectant selected from glycerin, diglycerin, and a combination thereof;
wherein the cetyl hydroxyethylcellulose and the sodium hyaluronate are interlaced; and
wherein the crosslinked gellan gum is crosslinked via ionic bonds, through the mono-, or di-valent ion, and entraps the interlaced cetyl hydroxyethylcellulose, the sodium hyaluronate, and the humectant to form the interpenetrating polymer network moisturizing topical composition.

5. The method of claim 4, wherein the mono-, or di-valent ion is selected from the group consisting of 2-Pyrrolidone-5-Carboxylic Acid (PCA), calcium PCA, sodium PCA, zinc PCA, magnesium PCA, sea salt, inorganic salts of citric acid, inorganic salts of lactic acid, calcium ascorbate, magnesium ascorbate, calcium oxide, calcium benzoate, calcium sorbate, calcium aspartate, magnesium carbonate, magnesium chloride, magnesium nitrate, and any combination thereof.

6. The method of claim 4, wherein the moisturizing composition is a formulation selected from the group consisting of liquid, solution, emulsion, suspension, triturate, jelly, foam, paste, ointment shampoo, adhesive, cream, serum, milk, lotion, salve, oil, butter, gel, and balm.

7. A method of producing a interpenetrating polymer network moisturizing topical composition, the method comprising:
dispersing a non-crosslinked gellan gum capable of crosslinking in water to form a first phase;
combining sodium hyaluronate and cetyl hydroxyethylcellulose with a humectant selected from glycerin, diglycerin, and a combination thereof to form a second phase;
combining the first and second phases to form a third phase of uncrosslinked interlaced gellan gum, sodium hyaluronate, and cetyl hydroxyethylcellulose;
adding a mono-valent, di-valent ion or a combination thereof to the third phase to crosslink the gellan gum to form the interpenetrating polymer network moisturizing topical composition,
wherein the interpenetrating polymer network moisturizing topical composition is made up of a crosslinked gellan gum in a three dimensional structure, sodium hyaluronate, cetyl hydroxyethylcellulose, and the humectant; wherein the crosslinked gellan gum entraps the interlaced sodium hyaluronate, cetyl hydroxyethylcellulose, and the humectant, and
wherein the crosslinked gellan gum is crosslinked via ionic bonds wherein the composition comprises
about 0.01% w/w to about 5% w/w of crosslinked gellan gum;
about 0.01% w/w to about 5% w/w of cetyl hydroxyethylcellulose;
about 0.01% w/w to about 5% w/w of sodium hyaluronate;
about 0.01% w/w to about 5% w/w of the mono-, or di-valent ion; and
about 25% w/w to about 80% w/w of the humectant.

8. The method of claim 7, the mono-valent, di-valent ion is selected from group consisting of 2-Pyrrolidone-5-Carboxylic Acid (PCA), calcium PCA, sodium PCA, zinc PCA, magnesium PCA, sea salt, inorganic salts of citric acid, inorganic salts of lactic acid, calcium ascorbate, magnesium ascorbate, calcium oxide, calcium benzoate, calcium sorbate, calcium aspartate, magnesium carbonate, magnesium chloride, magnesium nitrate, and any combination thereof.

9. A drug or active ingredient delivery system comprising:
about 0.01% w/w to about 5% w/w of crosslinked gellan gum;
about 0.01% w/w to about 5% w/w of cetyl hydroxyethylcellulose;
about 0.01% w/w to about 5% w/w of sodium hyaluronate;
about 0.01% w/w to about 5% w/w of a mono-, or di-valent ion;
about 25% w/w to about 80% w/w of a humectant selected from glycerin, diglycerin, and a combination thereof; and
a drug or active ingredient;
wherein the cetyl hydroxyethylcellulose and the sodium hyaluronate are interlaced; and
wherein the crosslinked gellan gum is crosslinked via ionic bonds, through the mono-, or di-valent ion, and entraps the cetyl hydroxyethylcellulose, the sodium hyaluronate, the humectant, and the drug or active ingredient to form the interpenetrating polymer network moisturizing topical composition.

10. The drug or active ingredient delivery system of claim 9, wherein the mono-, or di-valent ion is selected from the group consisting of 2-Pyrrolidone-5-Carboxylic Acid (PCA), calcium PCA, sodium PCA, zinc PCA, magnesium PCA, sea salt, inorganic salts of citric acid, inorganic salts of lactic acid, calcium ascorbate, magnesium ascorbate, calcium oxide, calcium benzoate, calcium sorbate, calcium aspartate, magnesium carbonate, magnesium chloride, magnesium nitrate, and any combination thereof.

11. The drug or active ingredient delivery system of claim 9, wherein the drug or active ingredient is selected from the group consisting of benzoyl peroxide, salicylic acid, willowbark extract, poly hydroxyacid, tannic acid, hydroxybenzoic acid, juniperic acid, tartaric acid, glycolic acid, lactic acid, citric acid, retinol, antioxidants, vitamin A, retinoid, tretinoin, tazarotene, ibuprofen, diclofenac, felbinac, ketoprofen, piroxicam and any combination thereof.

12. The moisturizing topical composition of claim 1, wherein the mono-, or di-valent ion is selected from calcium PCA, magnesium PCA, and combinations thereof.

13. The moisturizing topical composition of claim 1, wherein the humectant is in an amount of about 30%.

14. The moisturizing topical composition of claim 1, wherein the humectant is glycerin and is in an amount of about 30%.

15. The moisturizing topical composition of claim 1, wherein the viscosity of the moisturizing topical composition is about 400 to about 1400 cps.

16. The moisturizing topical composition of claim 1, wherein the gellan gum is in an amount of about 0.11% w/w, the cetyl hydroxyethylcellulose is in an amount of about 0.30% w/w, the sodium hyaluronate is in an amount of about 0.12% w/w, the mono-, or di-valent ion is a combination of magensium PCA in an amount of about 0.30% w/w and calcium PCA in an amount of about 0.30% w/w, and the humectant is glycerin in an amount of about 30% w/w.

* * * * *

UNITED STATES PATENT AND TRADEMARK OFFICE
CERTIFICATE OF CORRECTION

PATENT NO. : 10,722,443 B2
APPLICATION NO. : 15/430578
DATED : July 28, 2020
INVENTOR(S) : Kathy Ann Fields et al.

Page 1 of 1

It is certified that error appears in the above-identified patent and that said Letters Patent is hereby corrected as shown below:

On the Title Page

Item (60) should read:
Provisional application No. 62/394,540, filed on Sep. 14, 2016, provisional application No. 62/294,706 filed on Feb. 12, 2016.

Signed and Sealed this
Eighth Day of September, 2020

Andrei Iancu
*Director of the United States Patent and Trademark Office*